US012758302B2

(12) United States Patent
Boronyak et al.

(10) Patent No.: US 12,758,302 B2
(45) Date of Patent: Oct. 13, 2026

(54) ELECTROSURGICAL INSTRUMENT AND METHOD OF FREQUENCY MONITORING FOR SEALING TISSUE

(71) Applicant: Cilag GmbH International, Zug (CH)

(72) Inventors: Steven M. Boronyak, Cincinnati, OH (US); Terry D. McCoy, Hamilton, OH (US); Megan E. McKinley, Cincinnati, OH (US); Jeremy Chinwe Orie, Cincinnati, OH (US); Dylan Rushton, Novi, MI (US)

(73) Assignee: CILAG GMBH INTERNATIONAL, Zug (CH)

( * ) Notice: Subject to any disclaimer, the term of this patent is extended or adjusted under 35 U.S.C. 154(b) by 85 days.

(21) Appl. No.: 18/783,741

(22) Filed: Jul. 25, 2024

(65) Prior Publication Data

US 2026/0026865 A1 Jan. 29, 2026

(51) Int. Cl.

| | |
|---|---|
| ***A61B 18/12*** | (2006.01) |
| ***A61B 18/14*** | (2006.01) |
| *A61B 18/00* | (2006.01) |

(52) U.S. Cl.

CPC .. *A61B 18/1445* (2013.01); *A61B 2018/0063* (2013.01); *A61B 2018/00732* (2013.01); *A61B 2018/00827* (2013.01); *A61B 2018/00892* (2013.01); *A61B 2018/1273* (2013.01)

(58) Field of Classification Search

CPC ...... A61B 2018/00732; A61B 18/1233; A61B 2018/00869

See application file for complete search history.

(56) References Cited

U.S. PATENT DOCUMENTS

| | | | | |
|---|---|---|---|---|
| 5,931,836 | A * | 8/1999 | Hatta ................. | A61B 18/1206 606/45 |
| 6,783,524 | B2 | 8/2004 | Anderson et al. | |
| 8,986,302 | B2 | 3/2015 | Aldridge et al. | |
| 11,896,327 | B1 | 2/2024 | Aklivanh et al. | |
| 2007/0129726 | A1* | 6/2007 | Eder ................. | A61B 18/1442 606/49 |

(Continued)

FOREIGN PATENT DOCUMENTS

| | | | |
|---|---|---|---|
| WO | WO-9808479 A1 * | 3/1998 | ............. G05G 1/305 |

OTHER PUBLICATIONS

International Search Report and Written Opinion dated Dec. 9, 2025, for International Application No. PCT/IB2025/057393, 26 pages.

*Primary Examiner* — Jaymi E Della
(74) *Attorney, Agent, or Firm* — FBT Gibbons LLP

(57) ABSTRACT

A method for performing an electrosurgical procedure is provided. The method includes engaging a tissue with an electrode and applying a non-therapeutic signal to the tissue via the electrode. The method further includes varying a frequency of the non-therapeutic signal and receiving a return signal generated from the tissue in response to the non-therapeutic signal. The non-therapeutic signal includes a voltage and a current. The method further includes detecting a phase angle between the voltage and the current of the non-therapeutic signal during the varying of the frequency of the non-therapeutic signal, and identifying, as a center frequency, the frequency when the phase angle of the return signal is at a minimum. A surgical system is also provided.

20 Claims, 20 Drawing Sheets

(56) References Cited

U.S. PATENT DOCUMENTS

| | | | | |
|---|---|---|---|---|
| 2007/0252094 | A1* | 11/2007 | Ulrich | G03F 7/70275<br>359/364 |
| 2009/0048595 | A1 | 2/2009 | Mihori et al. | |
| 2017/0252094 | A1 | 9/2017 | Honda et al. | |
| 2022/0249002 | A1 | 8/2022 | Chapman et al. | |
| 2024/0000499 | A1* | 1/2024 | Lafay | A61B 18/1445 |
| 2024/0189015 | A1 | 6/2024 | Ramin et al. | |

* cited by examiner

ELECTROSURGICAL INSTRUMENT AND METHOD OF FREQUENCY MONITORING FOR SEALING TISSUE

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio.

However, ensuring an adequate and reliable tissue seal remains a significant challenge. If the seal is not properly formed, it can fail, leading to bleeding or leakage at the surgical site. Several factors influence the integrity and consistency of the tissue seal. The applied force, the tissue thickness, the moisture content of the tissue, and the delivery of energy must all be precisely controlled.

The thickness of the tissue bundle grasped between the jaws is particularly critical. If the tissue bundle is too thick, the jaws may not compress it sufficiently for proper seal formation. Conversely, if the tissue bundle is too thin, the tissue may desiccate or char before an adequate seal can form. Gauging the thickness of the compressed tissue bundle is difficult since it is obstructed from view between the closed jaws.

Additionally, variations in the tissue properties and composition can impact the heating and sealing process. Tissue with high fluid content will heat differently than drier tissue, affecting the energy requirements necessary to achieve proper sealing. Fatty tissues also behave differently than vascular tissues when energy is applied.

Given the often obstructed line of sight to the tissue being sealed and/or the heterogeneous tissue properties encountered, it is extremely difficult to confirm the quality and integrity of the resulting tissue seal. In some instances, the seal must be physically tested, by physically pulling on it which is obviously undesirable during a surgical procedure.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
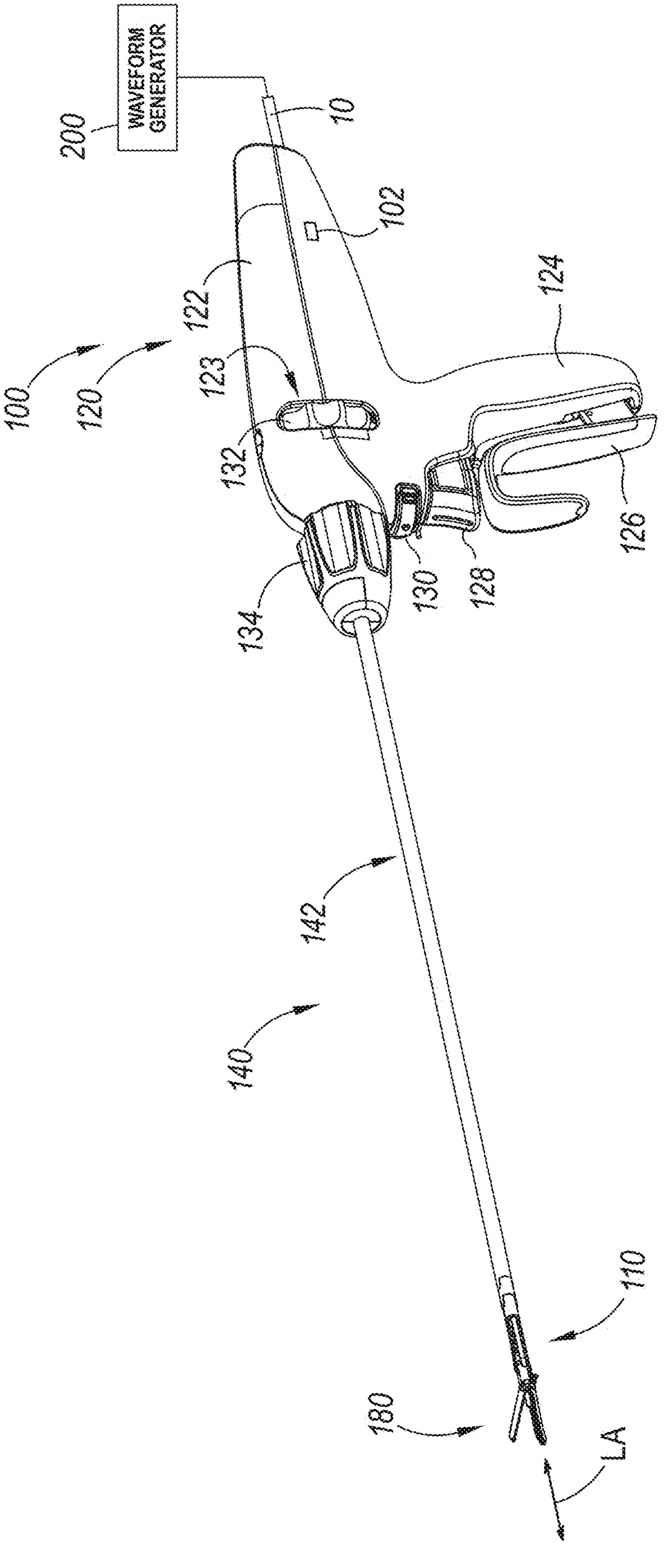
FIG. 1 depicts a perspective view of an exemplary electrosurgical instrument.
Figure 2:
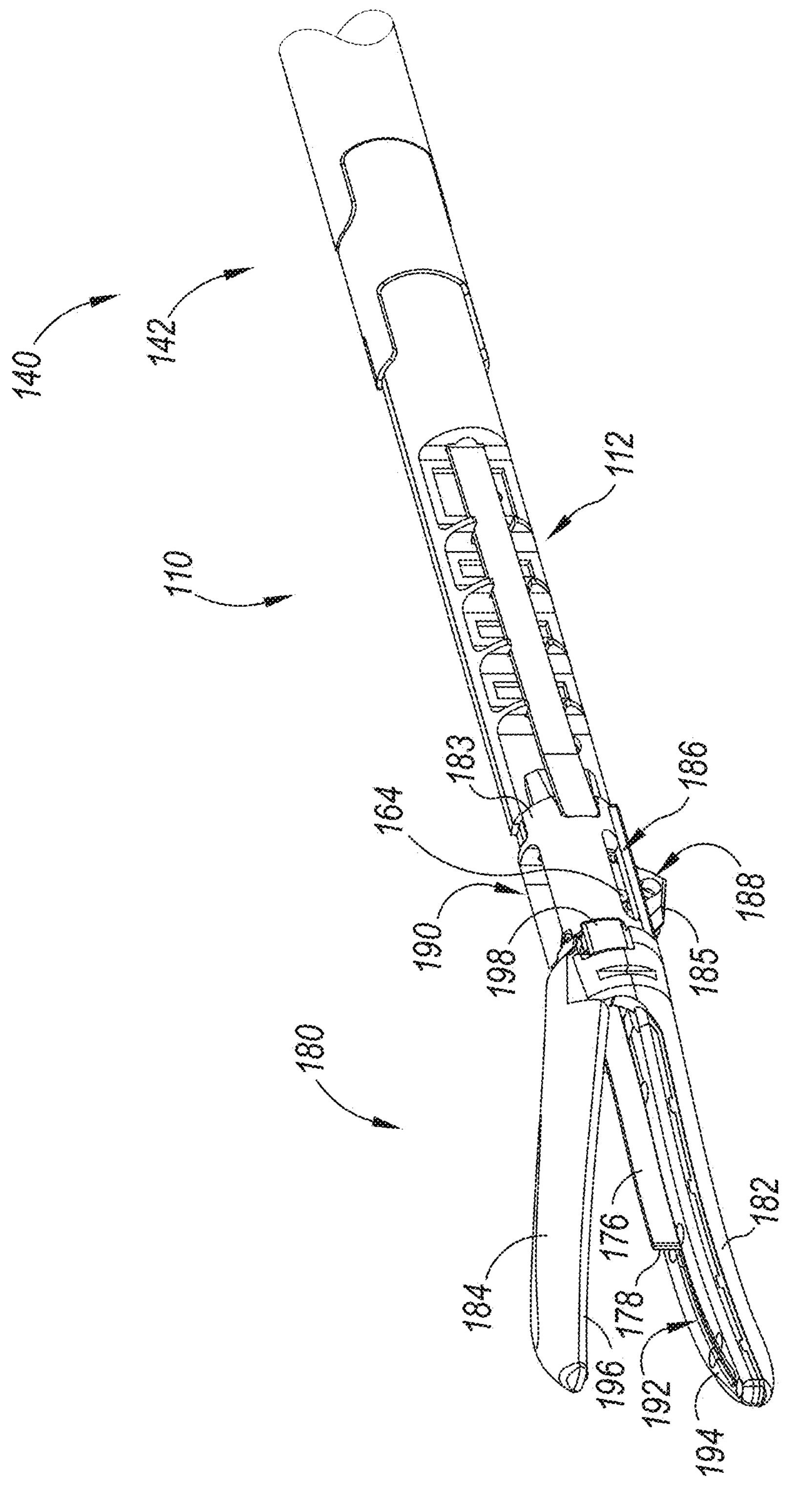
FIG. 2 depicts a perspective view of an exemplary articulation assembly and end effector of the electrosurgical instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms “proximal” and “distal” are defined herein relative to a surgeon or other operator grasping a surgical instrument having a distal surgical end effector. The term “proximal” refers the position of an element closer to the surgeon or other operator and the term “distal” refers to the position of an element closer to the surgical end effector of the surgical instrument and further away from the surgeon or other operator.

I. Example of Electrosurgical Instrument

FIGS. 1-5 show a surgical system (98) including an exemplary electrosurgical instrument (100). As best seen in FIG. 1, electrosurgical instrument (100) includes a handle assembly (120), a shaft assembly (140), an articulation assembly (110), which may also be referred to as an articulation section (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to apply a non-therapeutic bipolar radio frequency (RF) energy in order to identify and/or verify that the correct tissue is present in the end effector such that a therapeutic RF energy can be applied to seal or weld tissue. However, it should be understood that electrosurgical instrument (100) may be configured to seal or weld tissue through any other suitable means that would be apparent to one skilled in the art in view of the teachings herein. For example, electrosurgical instrument (100) may be configured to seal or weld tissue via an ultrasonic blade, staples, etc. In the present example, electrosurgical instrument (100) is electrically coupled to a waveform generator (200) of surgical system (98), which is capable of delivering therapeutic and non-therapeutic energy, via power cable (10).

Waveform generator (200) may be configured to provide all or some of the electrical power requirements for use of electrosurgical instrument (100). Any suitable waveform generator (200) may be used as would be apparent to one skilled in the art in view of the teachings herein. By way of non-limiting example, the waveform generator (200) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein, in its entirety. While in the current example, electrosurgical instrument (100) is coupled to waveform generator (200) via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one skilled in the art in view of the teaching herein.

Handle assembly (120) is configured to be grasped by an operator with one hand, such that an operator may control and manipulate electrosurgical instrument (100) with a single hand. Although electrosurgical instrument (100) is primarily described herein as being used by a human user, it should be noted that alternative versions exist in which one or more robotic systems (e.g., a robotic arm) may be used to control and manipulate electrosurgical instrument (100). Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. Articulation assembly (110) is configured to deflect end effector (180) from the longitudinal axis (LA) defined by shaft assembly (140).

Handle assembly (120) of the present example includes a control unit (102) housed within a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Additionally, knife trigger (128) may be pivoted toward and away from pistol grip (124) and/or body (122) to actuate a knife member (176) within the confines of jaws (182, 184) to cut tissue captured between jaws (182, 184). Further, activation button (130) may be pressed to apply radio frequency (RF) energy to tissue via electrodes (194, 196) of jaws (182, 184), respectively. In some versions, electrodes (194, 196) of jaws (182, 184) are in a bifurcation configuration where electrodes (194, 196) move relative to a central axis and nearly equal and opposite to one another.

Body (122) of handle assembly (120) defines an opening (123) through which a portion of articulation control (132) protrudes. Articulation control (132) is rotatably disposed within body (122) such that an operator may rotate the portion of articulation control (132) protruding from opening (123) to rotate the portion of articulation control (132) located within body (122). Rotation of articulation control (132) relative to body (122) will bend articulation assembly (110) in order to drive deflection of end effector (180) from the longitudinal axis (LA) defined by shaft assembly (140). Articulation control (132) and articulation assembly (110) may include any suitable features to drive deflection of end effector (180) from the longitudinal axis (LA) defined by shaft assembly (140) as would be apparent to one skilled in the art in view of the teachings herein.

Knob (134) is rotatably disposed on the distal end of body (122) and is configured to rotate end effector (180), articulation assembly (110), and shaft assembly (140) about the longitudinal axis (LA) of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one skilled in the art in view of the teachings herein.

Figure 3:
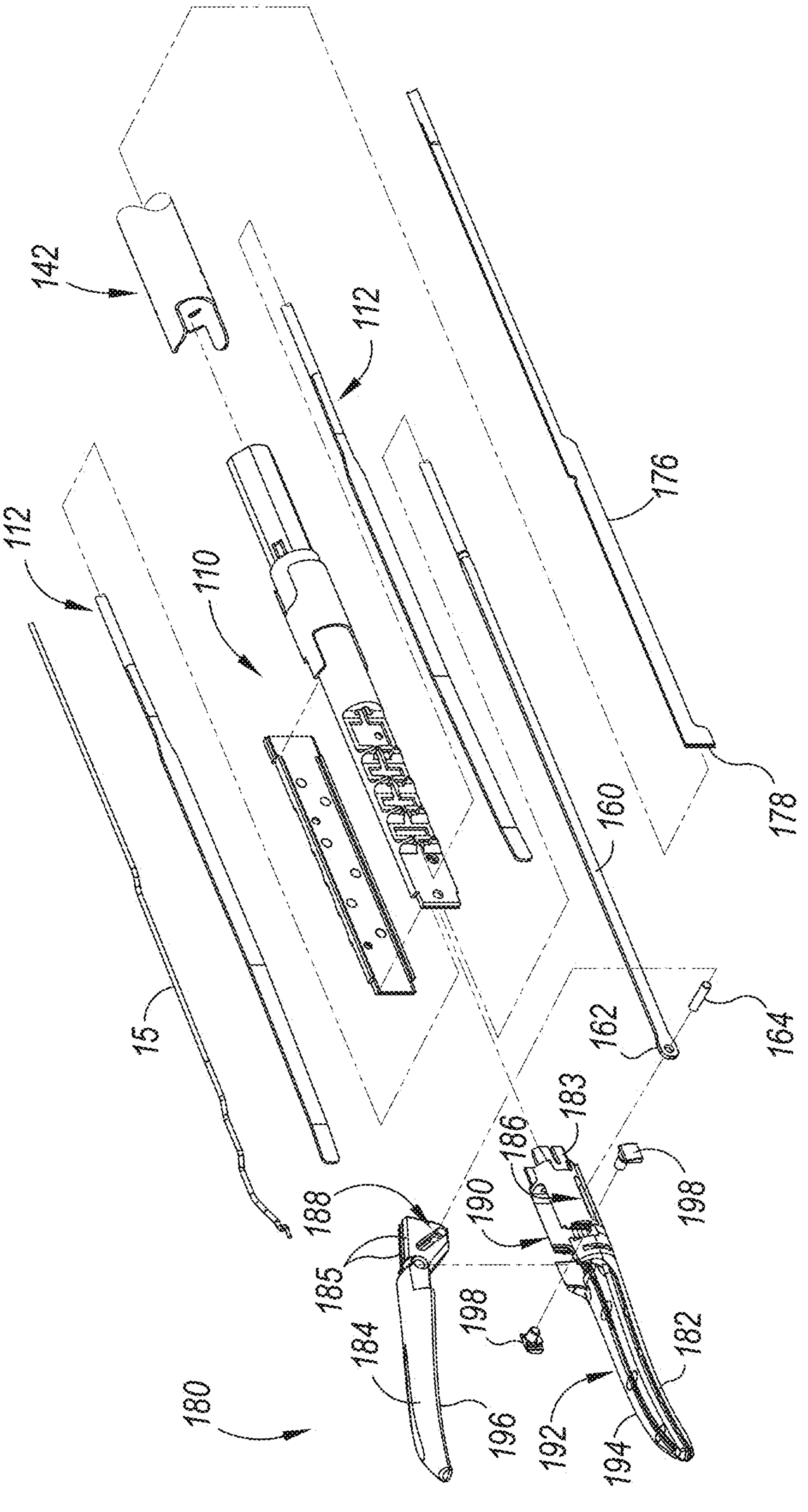
FIG. 3 depicts an exploded view of the articulation assembly and end effector of FIG. 2.
Figure 4:
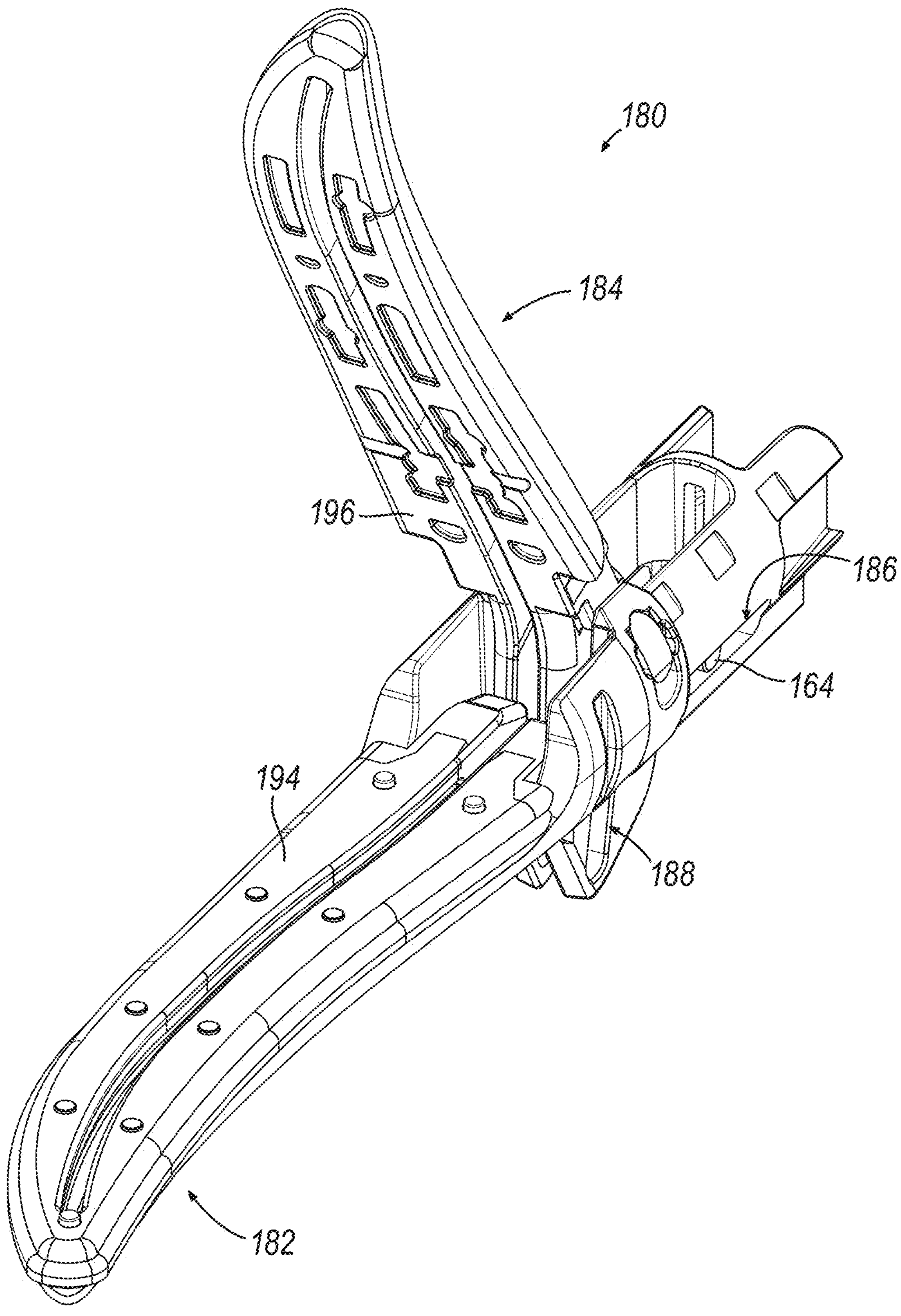
FIG. 4 depicts a perspective view of the end effector that of FIG. 2.
Figure 5:
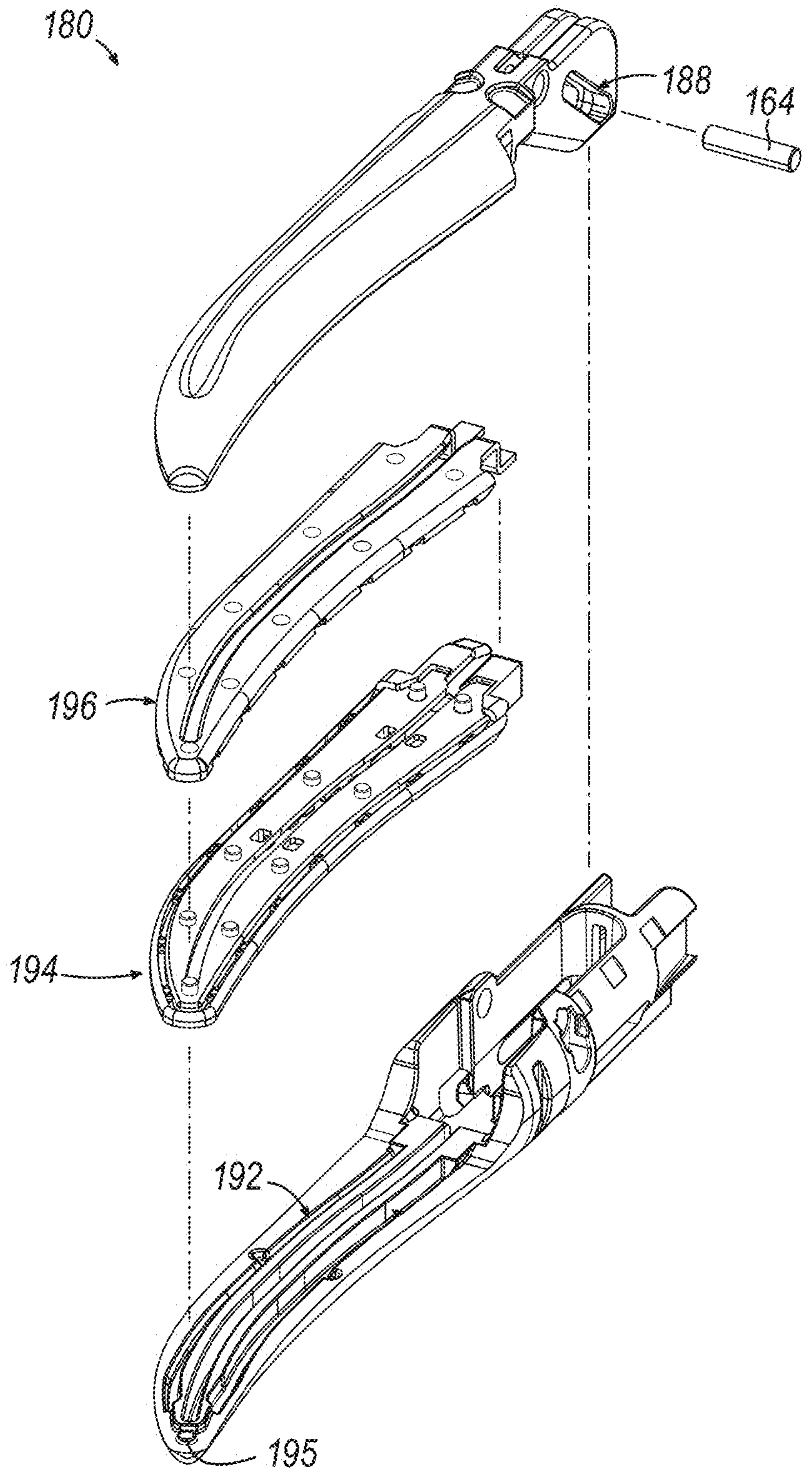
FIG. 5 depicts an exploded perspective view of the end effector of FIG. 2.

Shaft assembly (140) includes distal portion (142) extending distally from handle assembly (120) and a proximal portion housed within the confines of body (122) of handle assembly (120). Referring to FIG. 3, shaft assembly (140) houses a jaw closure connector (160) that couples jaw closure trigger (126) with end effector (180). Additionally, shaft assembly (140) houses a portion of knife member (176) extending between distal a distal cutting edge (178) of knife member (176) and knife trigger (128). Shaft assembly (140) also houses actuating members (112) that couple articulation assembly (110) with articulation control (132); as well as an electrical coupling (15) that operatively couples electrodes (194, 196) with activation button (130). As will be described in greater detail below, jaw closure connector (160) is configured to translate relative to shaft assembly (140) to open and close jaws (182, 184) of end effector (180); while knife member (176) is coupled to knife trigger (128) of handle assembly (120) to translate distal cutting edge (178) within the confines of end effector (180); and activation button (130) is configured to activate electrodes (194, 196).

As best seen in FIGS. 2-5, end effector (180) includes lower jaw (182) pivotally coupled with upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (176), jaw closure connector (160), and pin (164). Slots (186, 188) each slidably receive pin (164), which is attached to a distal coupling portion (162) of jaw closure connector (160). Additionally, lower jaw (182) includes a force sensor (195) located at a distal tip of lower jaw (182), though force sensor (195) may alternatively be positioned at any other suitable location. Force sensor (195) may be in communication with control unit (102). Force sensor (195) may be configured to measure the closure force generated by pivoting jaws (182, 184) into a closed configuration in accordance with the description herein. Additionally, force sensor (195) may communicate this data to control unit (102). Any suitable components may be used for force sensor (195) as would be apparent to one skilled in art in view of the teachings herein. For example, force sensor (195) may take the form of a strain gauge. In some variations, end effector (180) includes more than one force sensor.

While in the current example, a force sensor (195) is incorporated into electrosurgical instrument (100) and is in communication with control unit (102), any other suitable sensors or feedback mechanisms may be additionally or alternatively incorporated into electrosurgical instrument (100) while in communication with control unit (102) as would be apparent to one skilled in the art in view of the teachings herein. For instance, an articulation sensor or feedback mechanism may be incorporated into electrosurgical instrument (100), where the articulation sensor communicates signals to control unit (102) indicative of the degree end effector 180 is deflected from the longitudinal axis (LA) by articulation control (132) and articulation assembly (110).

As will be described in greater detail below, jaw closure connector (160) is operable to translate within central channel (190) of lower jaw (182). Translation of jaw closure connector (160) drives pin (164). As will also be described in greater detail below, with pin (164) being located within both slots (186, 188), and with slots (186, 188) being angled relative to each other, pin (164) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis and may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one skilled in the art in view of the teachings herein.

Lower jaw (182) and upper jaw (184) also define a knife pathway (192). Knife pathway (192) is configured to slidably receive knife member (176), such that knife member (176) may be retracted, and advanced, to cut tissue captured between jaws (182, 184).

Lower jaw (182) and upper jaw (184) each comprise a respective electrode (194, 196). The power source may provide RF energy to electrodes (194, 196) via electrical coupling (15) that extends through handle assembly (120), shaft assembly (140), articulation assembly (110), and electrically couples with one or both of electrodes (194, 196). Electrical coupling (15) may selectively activate electrodes (194, 196) in response to an operator pressing activation button (130). In some instances, control unit (102) may couple electrical coupling (15) with activation button (130), such that control unit (102) activates electrodes (194, 196) in response to operator pressing activation button (130). Control unit (102) may have any suitable components in order to perform suitable functions as would be apparent to one skilled in the art in view of the teachings herein. For instance, control unit (102) may have a processor, memory unit, suitable circuitry, etc. Examples of features and functionalities that may be incorporated into control unit (102) will be described in greater detail below.

As described above, jaw closure trigger (126) may be pivoted toward and away from pistol grip (124) and/or body (122) to open and close jaws (182, 184) of end effector (180) to grasp tissue. In particular, as will be described in greater detail below, pivoting jaw closure trigger (126) toward pistol grip (124) may proximally actuate jaw closure connector (160) and pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

In some versions, knife trigger (128) may be pivoted toward and away from body (122) and/or pistol grip (124) to actuate knife member (176) within knife pathway (192) of jaws (182, 184) to cut tissue captured between jaws (182, 184). In particular, handle assembly (120) further includes a knife coupling body that is slidably coupled along proximal portion of shaft assembly (140). Knife coupling body is coupled with knife member (176) such that translation of knife coupling body relative to proximal portion of shaft assembly (140) translates knife member (176) relative to shaft assembly (140).

In another version, knife coupling body may be coupled to a knife actuation assembly such that as knife trigger (128) pivots toward body (122) and/or pistol grip (124), knife actuation assembly drives knife coupling body distally, thereby driving knife member (176) distally within knife pathway (192). Because knife coupling body is coupled to knife member (176), knife member (176) translates distally within shaft assembly (140), articulation assembly (110), and within knife pathway (192) of end effector (180). Knife member (176) includes distal cutting edge (178) that is configured to sever tissue captured between jaws (182, 184). Therefore, pivoting knife trigger (128) causes knife member (176) to actuate within knife pathway (192) of end effector (180) to sever tissue captured between jaws (182, 184).

With distal cutting edge (178) of knife member (176) actuated to the advanced position, an operator may press activation button (130) to selectively activate electrodes (194, 196) of jaws (182, 184) to seal or weld severed tissue captured between jaws (182, 184). It should be understood that the operator may also press activation button (130) to selectively activate electrodes (194, 196) of jaws (182, 184) at any suitable time during exemplary use. Therefore, the operator may also press activation button (130) while knife member (176) is retracted. Next, the operator may release jaw closure trigger (126) such that jaws (182, 184) pivot into the opened configuration, releasing tissue.

II. Sensing Tissue Impedance for Determinations of Tissue State

Electrosurgical instrument (100) discussed above is configured to clamp tissue using end effector (180). Once securely clamped, electrodes (194, 196) in end effector (180) apply non-therapeutic energy in the form of a low voltage waveform to the tissue; and sensor devices measure the return signal (i.e., the waveform) to calculate and measure the impedance and reactance of the tissue. In one example, one or more electrodes (194, 196) are operatively connected to such sensor devices such that electrodes (194, 196) may be referred to as sensors in this respect. More specifically, electrosurgical instrument (100), via one or more sub-circuits, will provide non-therapeutic energy to the extra-cellular and intracellular fluid present within a given (e.g., clamped) region of tissue to determine an impedance of the tissue within jaws (182, 184). A processor may then relay information associated with the impedance and reactance. Using this associated information, a system inclusive of such electrosurgical instrument (100) cannot only identify the impedance and reactance of the tissue clamped between jaws (182, 184), but can also determine the optimal signal characteristics for the therapeutic signal and/or if a proper seal has been created after applying the therapeutic RF energy.

Figure 6:
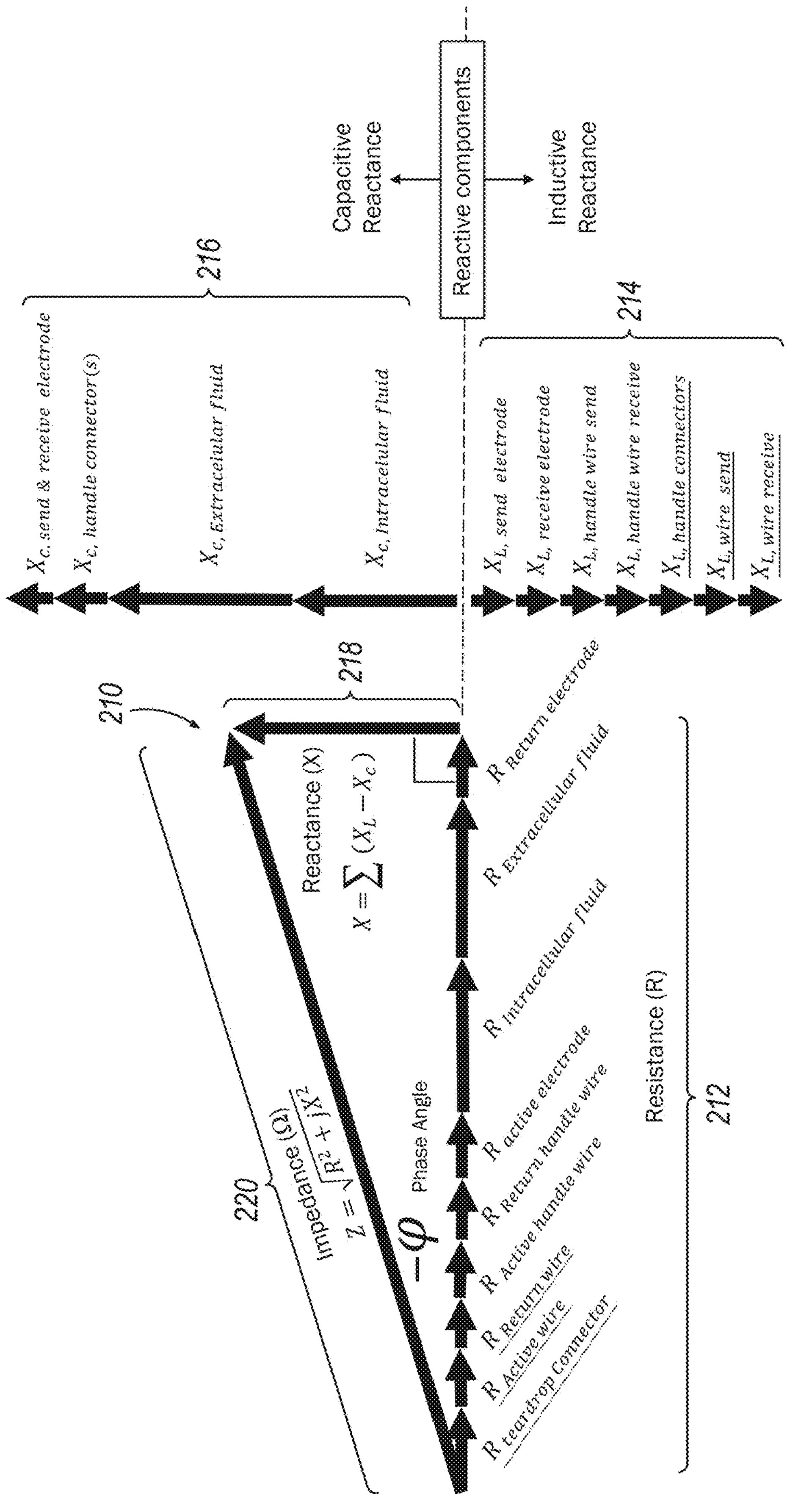
FIG. 6 depicts an illustrative impedance triangle.

FIG. 6 shows an illustrative impedance triangle (210). As would be understood by one skilled in the art, human tissues may tend to be capacitive in nature, while wires, tool, staples, implants, etc. may tend to be inductive in nature. Thus, as can be seen by the illustrative impedance triangle (210), the "resistance" of each object in the circuit is measured (212) using the waveform and sensor electrodes (194, 196). Such system can also determine the "capacitive reactance" of each object in the circuit and the inductive reactance of each object in the circuit. For example, the send and receive electrodes (194, 196), the send and receive handle wires, the handle connector and the send and receive wires (e.g., included in power cable 10 (see FIG. 1)) all have inductive reactance (214). Additionally, the send and receive electrodes (194, 196), the handle connector, the extracellular fluid, and the intracellular fluid all have capacitive reactance (216). The "reactance" (218) can then be calculated by determining the difference between the capacitive reactance and the inductive reactance using:

$$X = \sum (X_L - X_C). \quad \text{Equation 1}$$

As shown in FIG. 6, the "impedance" 1406 can then be determined using:

$$Z = \sqrt{R^2 + jX^2} \quad \text{Equation 2}$$

Figure 7:
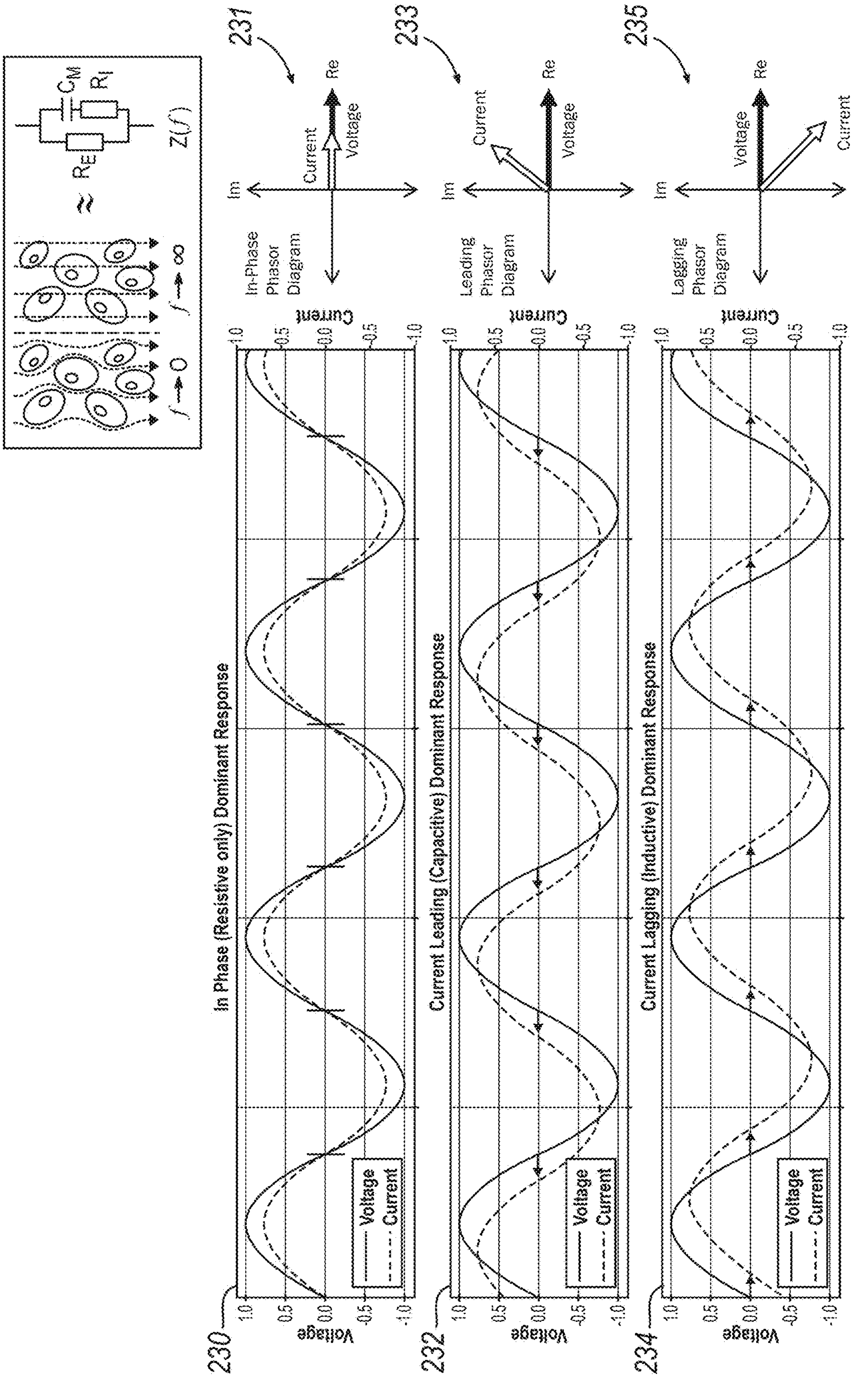
FIG. 7 depicts a set of illustrative example waveforms.

FIG. 7 shows a set of illustrative example waveforms. As would be understood by one skilled in the art, if a circuit only contains resistive items, the current and voltage will remain in phase such as shown in a first graph (230) and a first phasor diagram (231). Alternatively, if the circuit has capacitive objects, or more capacitive than inductive, the voltage wave will lead the current wave such as shown in a second graph (232) and a second phasor diagram (233). Finally, if the circuit has inductive objects, or more inductive objects than capacitive objects, the voltage will lag behind the current, such as shown in a third graph (234) and third phasor diagram (235).

Figure 8:
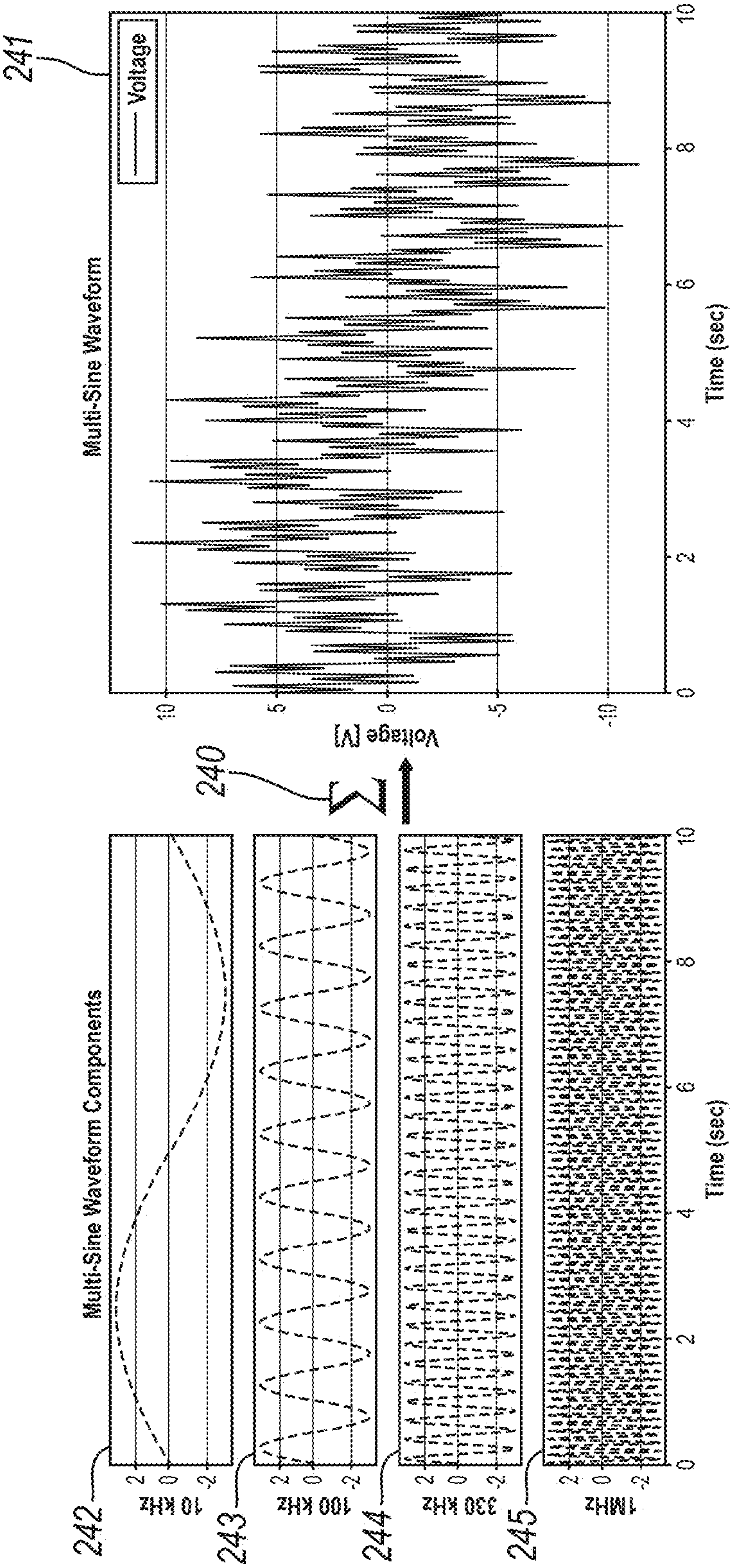
FIG. 8 depicts another set of illustrative example waveforms.

As discussed herein, the system may pass a non-therapeutic waveform through a portion of patient tissue to help identify the type of tissue as well as any foreign objects. Thus, in some versions, the system may pass waveforms of varying frequency (e.g., in series and/or parallel) to improve the accuracy of the determination. Accordingly, in some versions, and as shown in FIG. 8, multiple waveforms of various frequencies may be added or summed together (240) to create a multi-sine waveform (241). By way of non-limiting example, a 10 kHz sine wave (242) may be combined with a 100 kHz sine wave (243), a 330 kHz sine wave (244) and a 1 MHz sine wave (245) may be combined to create multi-sine wave (241).

Figure 9:
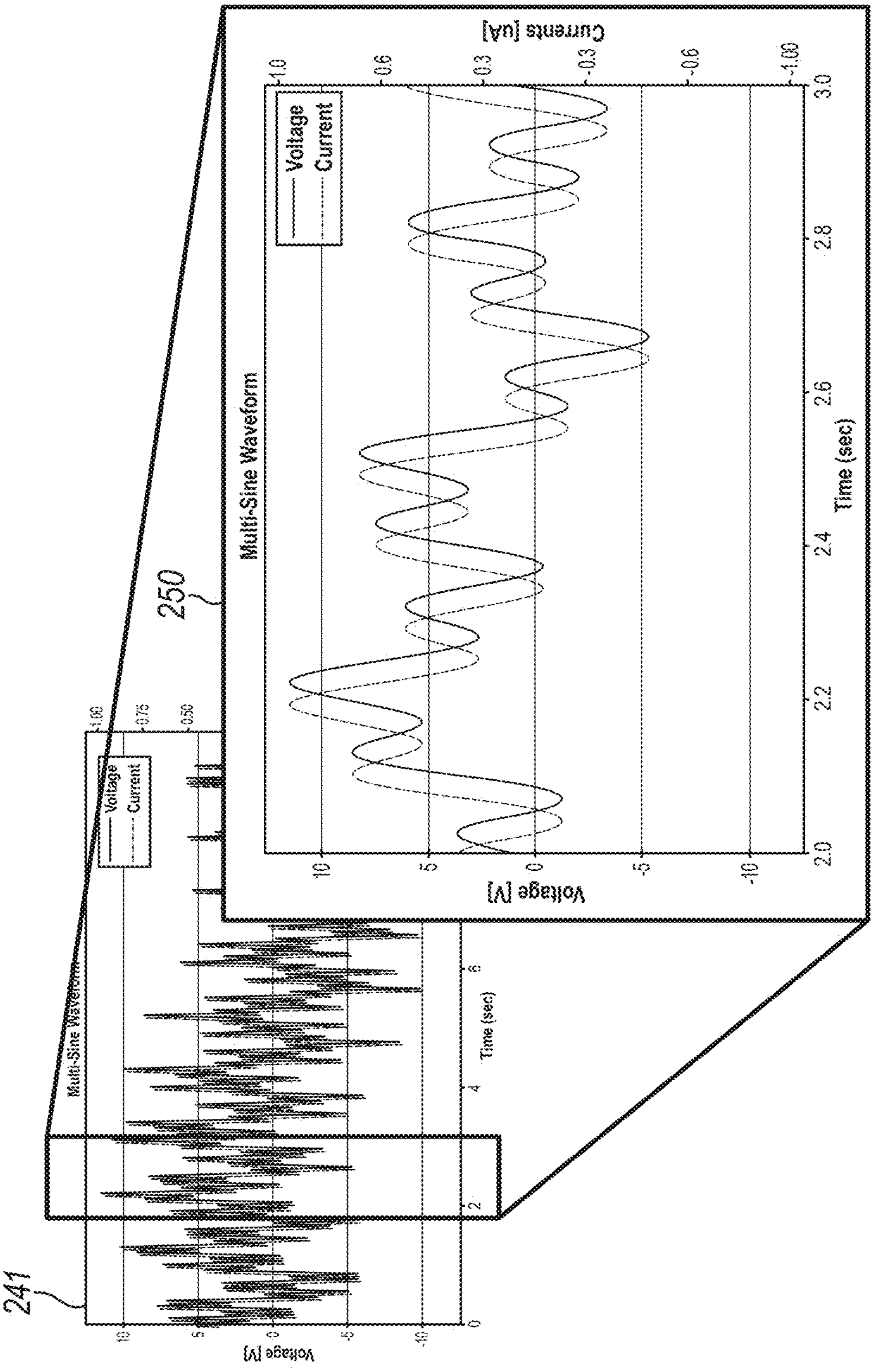
FIG. 9 depicts another illustrative example waveform.

Referring now to FIG. 9, multi-sine waveform (241) may be sampled or windowed. In some versions, such as those that require the use of Fast Fourier Transforms (FFT), the windowing or sampling may be as small as a single period for the lower frequency waveform. As shown in a fourth graph (250), the voltage of multi-sine waveform (241) is leading the current and thus in the present version indicates a capacitive circuit (e.g., likely tissue). In an alternative version, the system may apply a series of burst waveforms having different frequencies.

Figure 10:
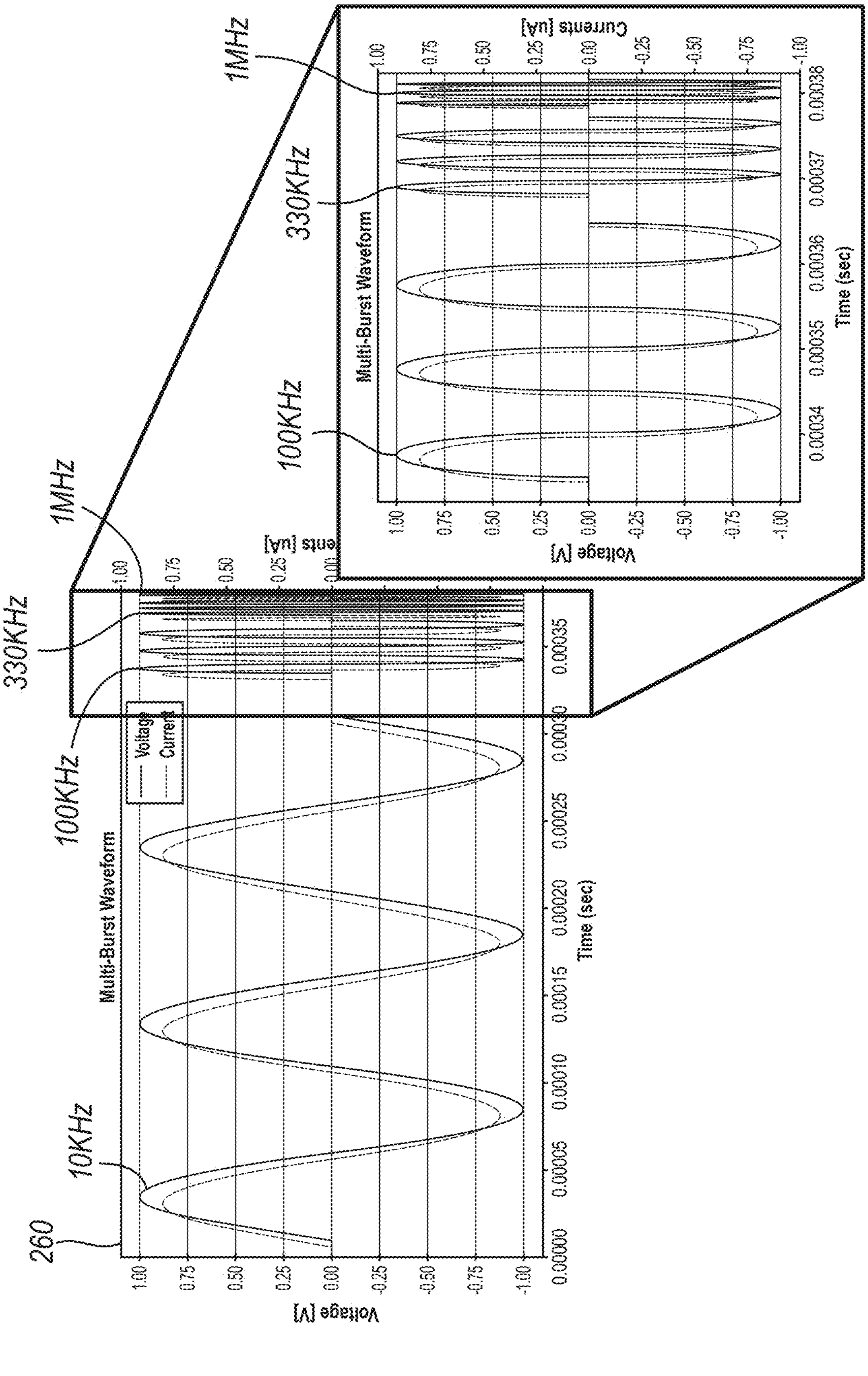
FIG. 10 depicts another illustrative example waveform.

Referring now to FIG. 10, a burst waveform, including a brief delay between frequencies, is shown in fifth graph (260). In some versions, and as shown, the system may output a burst waveform that is a sine wave, while in other versions, the wave may be a square, triangle, ramp, pulse, pseudorandom binary sequence (PRBS), or arbitrary waveform. In some versions, the pause between waveforms can be evaluated in order to determine a "rebounding" time. The rebounding time may be used to help identify tissue types by evaluating how long certain tissues take to allow the waveform and any residual energy to dissipate from the tissue.

Figure 11:
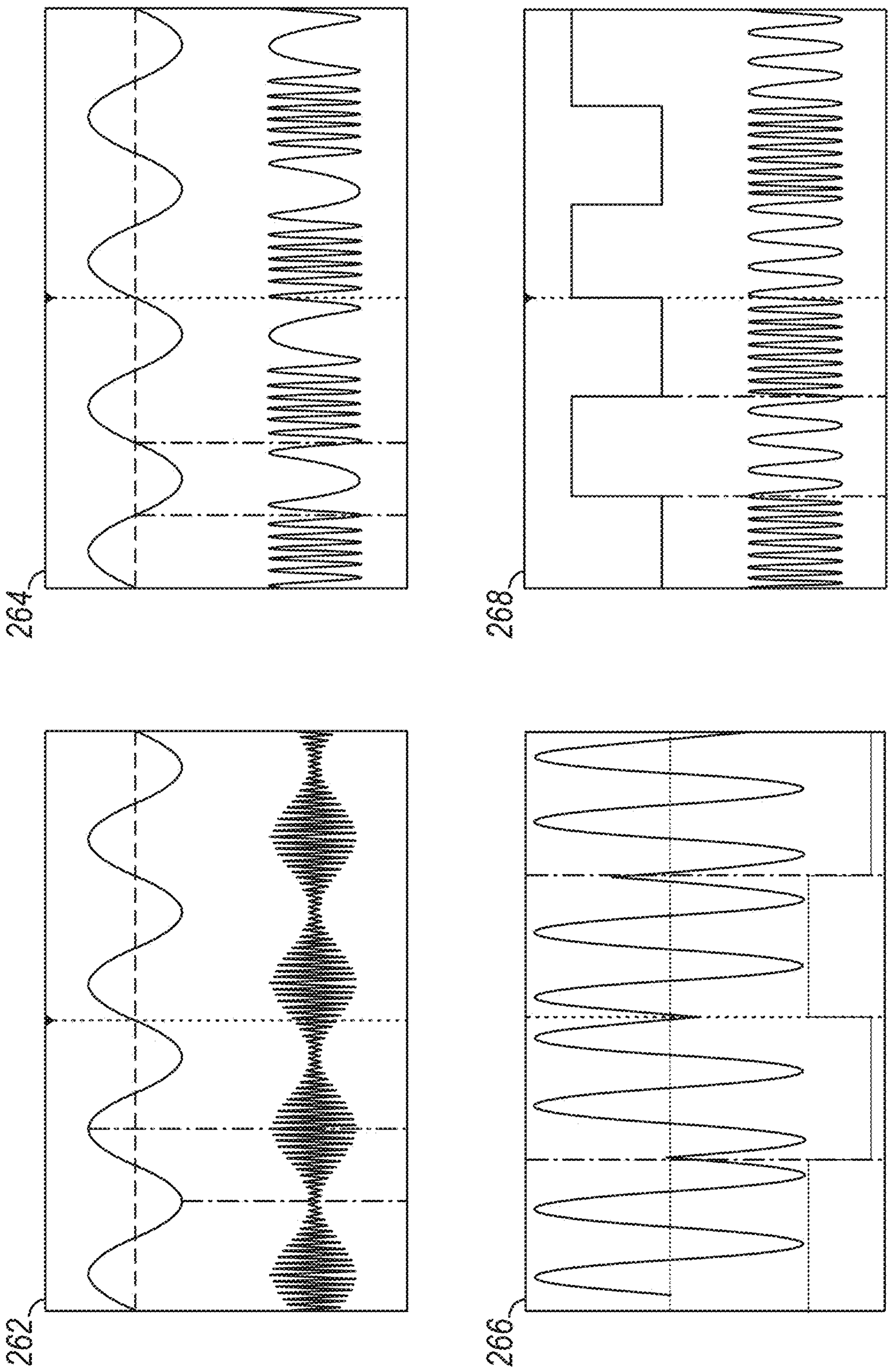
FIG. 11 depicts another set of illustrative example waveforms.

FIG. 11 shows various alternative burst versions. Specifically, in one version, amplitude modulation (AM) (262) may be used; while in another version, frequency modulation (FM) (264). Other versions may use phase modulation (PM) (266) and/or frequency-shift keying (FSK) modulation (268). Due to the fact that all of the modulation options shown in FIG. 11 involve a shift of some type, they may all be evaluated in a similar manner.

Figure 12:
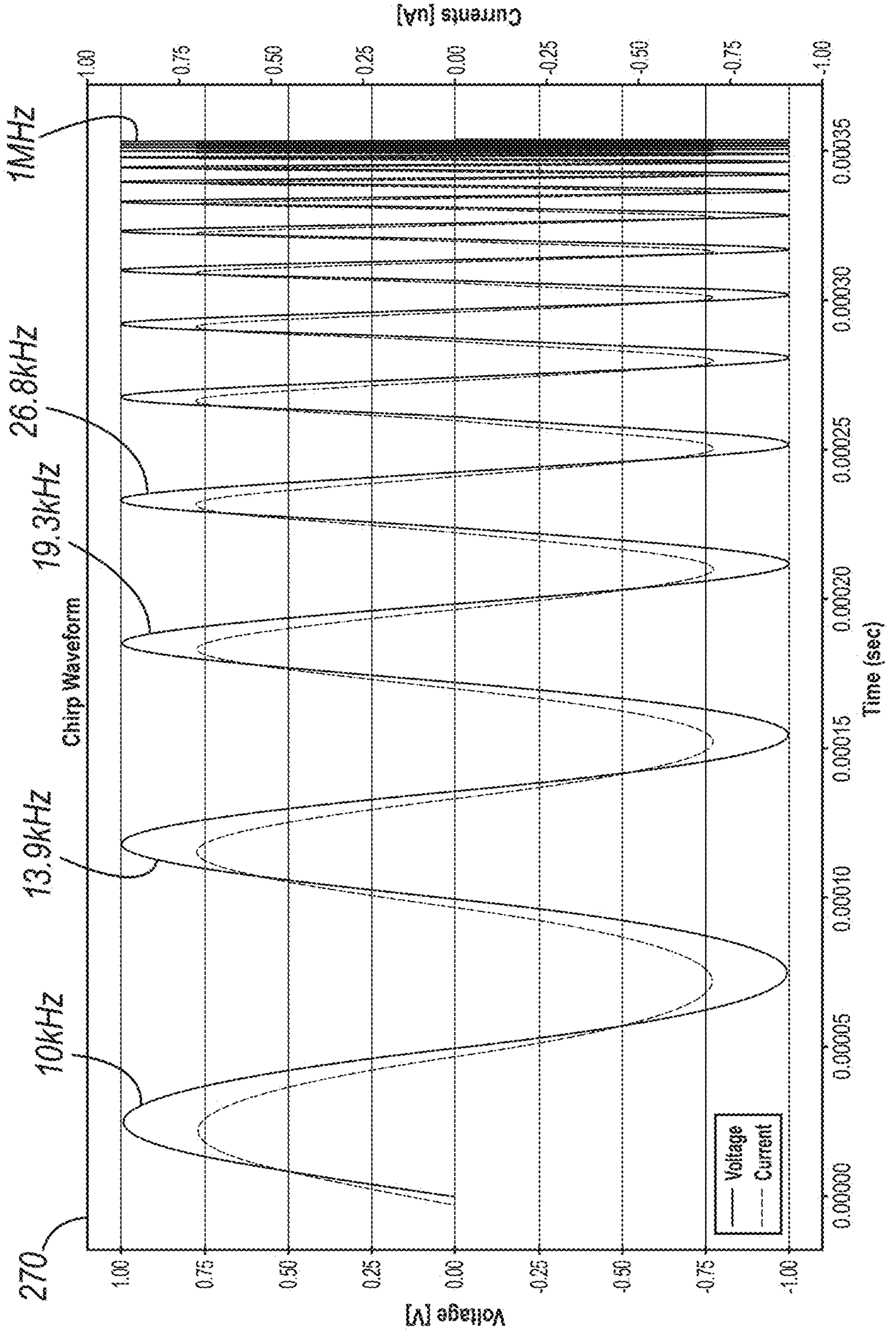
FIG. 12 depicts another illustrative example waveform.
Figure 13:
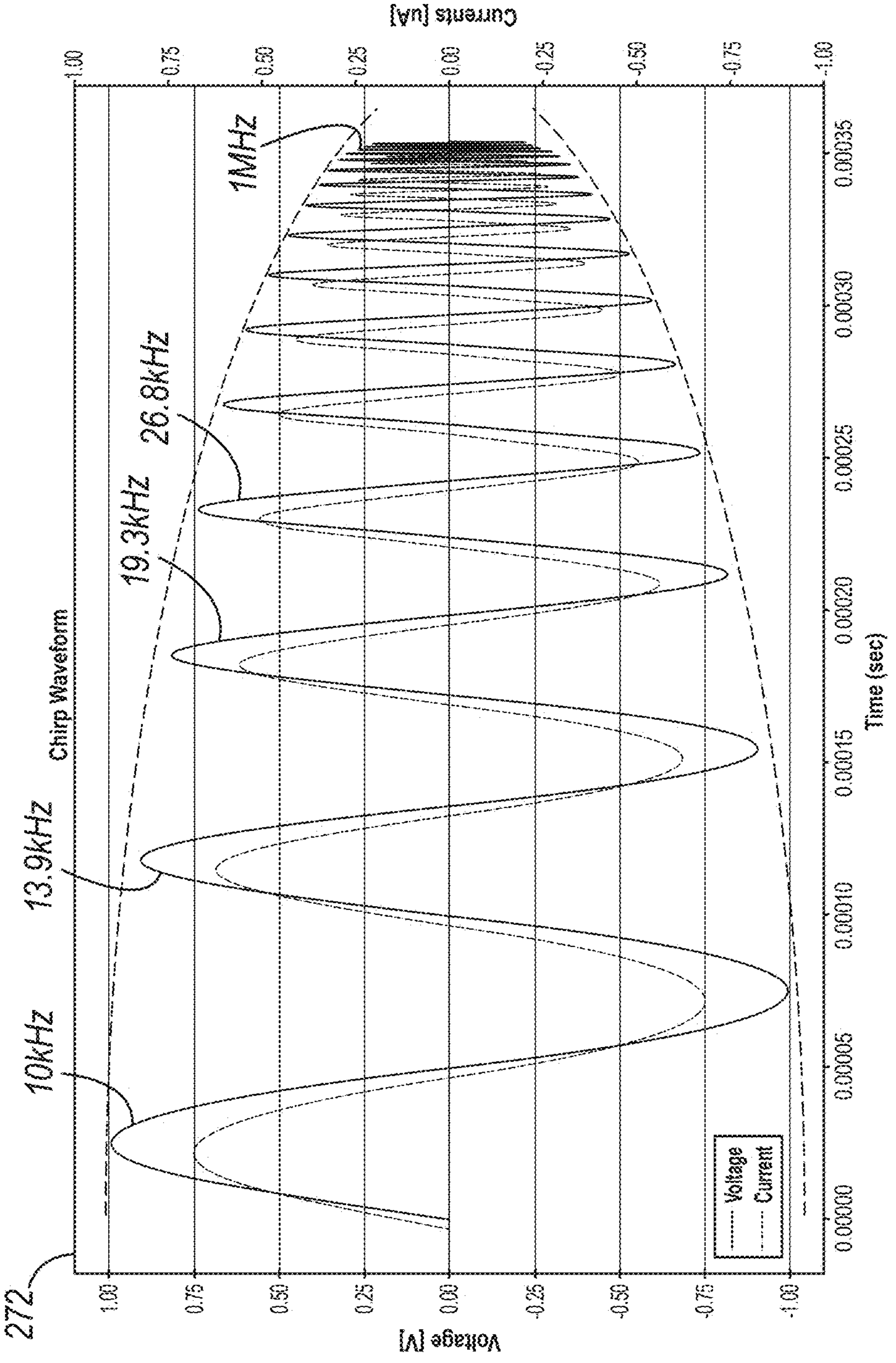
FIG. 13 depicts another illustrative example waveform.

In a further version, a "chirp" function can be used, such as shown in FIG. 12. As would be understood by one skilled in the art, a chirp wave can be an "up-chirp" (i.e., the frequency increases) or a "down-chirp" (i.e., the frequency decreases). Thus, stated differently, a chirp function is essentially an advanced form of FM (264). The chirp function shown in a sixth graph (270) shows a chirp waveform with increasing frequency (e.g., 10 kHz, 13.2 kHz, 19.3 kHz, 26.8 kHz, and 1 Mhz). FIG. 13 shows a seventh graph (272) depicting a chirp function with the same frequencies as shown in FIG. 12, but with a decreasing amplitude. Additional features associated with electrical circuits and measurements of tissue are described in U.S. patent application Ser. No. 17/854,306, entitled "Electrosurgical Instrument for Applying Non-Therapeutic RF Signals," filed Jun. 30, 2022, and published as U.S. Pat. Pub. No. 2024/0000499 on Jan. 4, 2024, the disclosure of which is incorporated by reference herein, in its entirety.

III. Applying Non-Therapeutic Signal with Frequency Sweep to Identify Center Frequency of System Achieving an effective and reliable tissue seal when applying a therapeutic signal to tissue during a procedure with an endocutter can be a significant challenge. The impedance of the tissue being sealed can vary substantially depending on the type of tissue, its vascularity, thickness, and other factors. If the therapeutic signal is not properly tailored for the impedance of the tissue, issues can arise. For example, if the therapeutic signal is too high relative to the tissue impedance, excessive heating and desiccation of the tissue can occur, leading to charring, smoking, and an increased risk of the seal failing. Conversely, if the RF signal is too low, inadequate heating may result in an incomplete seal with the potential for bleeding. It can therefore be desirable to first interrogate clamped tissue with a non-therapeutic signal prior to delivering a therapeutic signal to determine the impedance of the tissue and to subsequently tailor the therapeutic signal based upon the sensed impedance.

Even still, the impedance (i.e., the capacitance) of the tissue can change during sealing which means that the initial settings of the therapeutic signal might be somewhat inadequate as the seal nears completion. As a result, a surgeon oftentimes relies on their intuition regarding the proper amount of time and/or power that is required to apply the therapeutic signal to achieve an effective seal. This can sometimes lead to inconsistencies in the application of the therapeutic signal which can sometimes result in inadequate or unreliable sealing which can cause the seal to be susceptible to leaking or in some cases even rupturing. Because it is difficult for a surgeon to accurately determine whether the tissue seal is adequate after sealing, it may therefore be desirable to interrogate the tissue with a non-therapeutic signal during and/or after sealing to monitor the integrity of the seal. The following description relates to various examples of applying a non-therapeutic signal for determining the impedance of the tissue prior to, during, and/or after application of a therapeutic to enhance the integrity of a seal.

Generally speaking, the overall impedance of the system (i.e., the tissue and the device(s)) can have a reactance component that might be more or less capacitive or inductive depending on the properties of the tissue and the devices. When a signal is applied to the system, the reactance of the system can be determined from the phase angle between the voltage and current waveforms of the return signal (e.g., the voltage response and the current response of the system). When the phase angle of the voltage and current of the return signal is negative (meaning the voltage is leading the current), the system can be understood to be capacitive by a magnitude that is proportional to the magnitude of the phase angle. When the phase angle of the voltage and current of the return signal is positive (meaning the voltage is lagging the current), the system can be understood to be inductive by a magnitude that is proportional to the magnitude of the phase angle.

Figure 14:
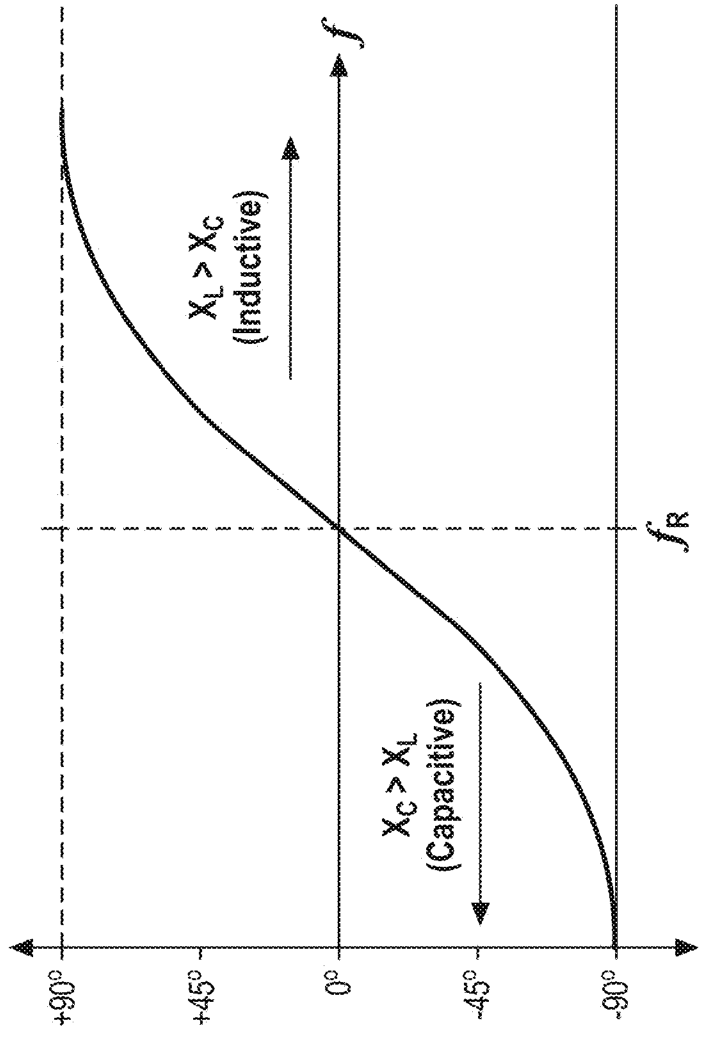
FIG. 14 depicts an example graph of the relationship between a frequency of a signal that is applied to tissue and a phase angle of a return signal of the applied signal.

The reactance of the system, however, can also be frequency dependent such that an increase in frequency of an applied signal increases the relative capacitance of the system. FIG. 14 illustrates an example of the relationship between the phase angle of the return signal and the frequency of the applied signal. As shown, as the frequency of the applied signal increases, the capacitive reactance of the system can decrease which can cause the system to become more inductive. When the phase angle of the voltage and current is between-90 degrees and 0 degrees (meaning the voltage is leading the current), an increase in frequency can decrease the overall capacitance of the system. When the phase angle of the voltage and current is between 90 degrees and 0 degrees (meaning the voltage is lagging the current), an increase in frequency can decrease the capacitance which increases the overall inductance of the system. When the phase angle between the voltage and current is at a minimum (e.g., at zero degrees-meaning the voltage and current are in phase), as indicated by the center frequency fr, the capacitive and inductive reactances from the tissue and the device(s) effectively cancel each other out such that the system is completely resistive. Therefore, at this center frequency, the reactance component of the impedance of the system can be at a minimum such that the tissue is most receptive to current flow. As a result, when a therapeutic signal is applied to the tissue at or near the center frequency, the overall quality of tissue seal can be enhanced.

In one version, when the tissue is initially clamped within jaws (182, 184), the non-therapeutic signal can be applied to the system to determine the center frequency of the system. During application of the non-therapeutic signal, the frequency of the signal can be varied (i.e., swept) along a range to effectively interrogate the frequency response of the tissue over that range. The frequency of the non-therapeutic signal can be varied by conducting a frequency sweep such as in the examples described above or below or by using any of a variety of suitable alternative techniques. The voltage and current of the non-therapeutic signal can remain substantially constant.

During variation of the frequency of the applied non-therapeutic signal, the phase angle of the returning waveform can be analyzed by the system and the frequency at which the phase angle is a minimum (e.g., zero) can be understood to be the center frequency. Once the center frequency is determined, it can then be used to generate the therapeutic signal as well as to determine the effectiveness of the resulting tissue seal, as will be described further below.

Figure 15:
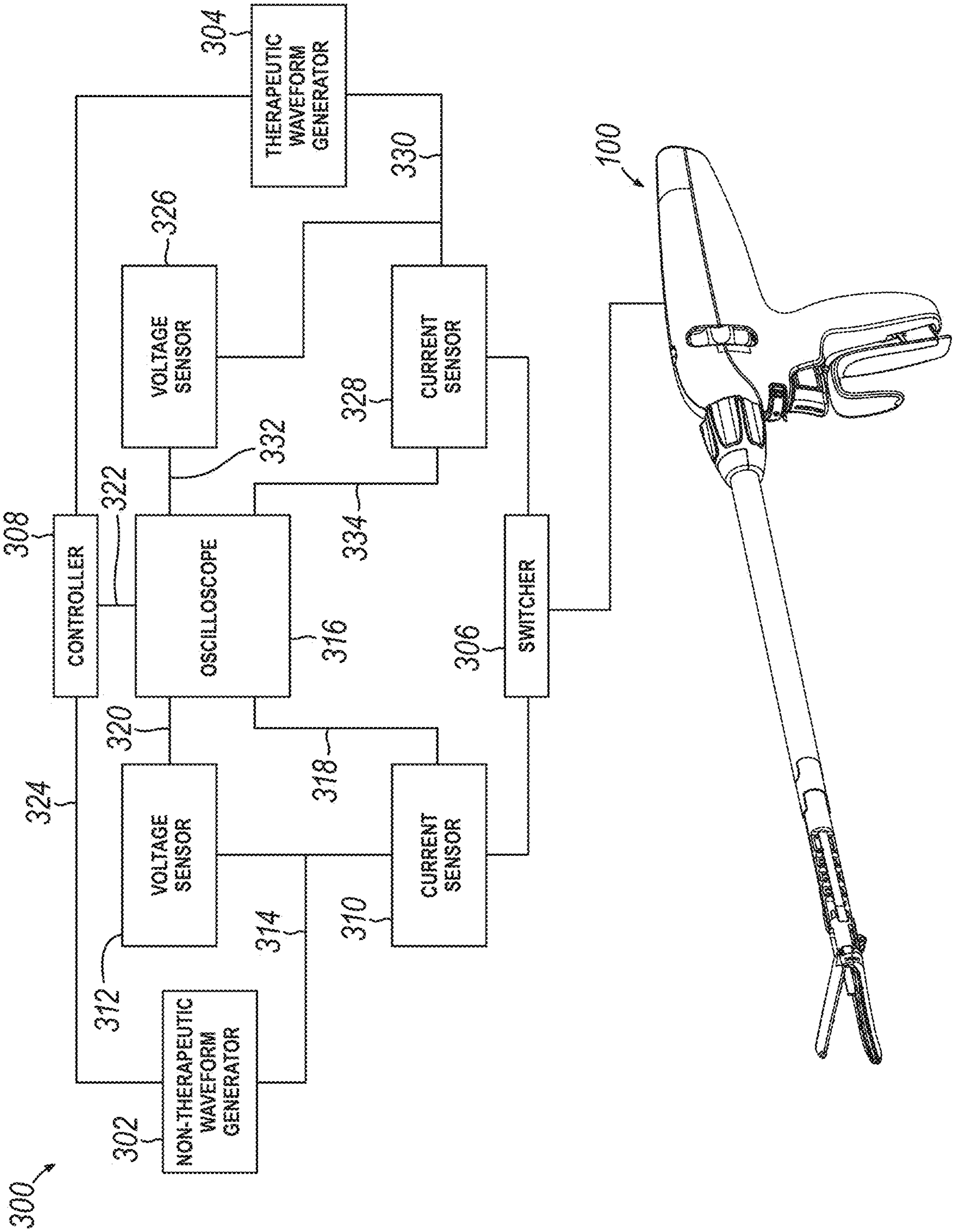
FIG. 15 depicts an Electrical Impedance Spectroscopy (EIS) system, in accordance with one embodiment.

A. Illustrative System for Applying Non-Therapeutic Signal with Frequency Sweep to Identify Center Frequency of System FIG. 15 shows an Electrical Impedance Spectroscopy (EIS) system (300) that is associated with electrosurgical instrument (100), illustrated in FIGS. 1-5, and is configured to coordinate the generation and application of the non-therapeutic and therapeutic signals onto tissue. EIS system (300) includes a non-therapeutic waveform generator (302) and a therapeutic waveform generator (304) that are configured to deliver the non-therapeutic and therapeutic signals, respectively, to electrosurgical instrument (100). The non-therapeutic signal discussed herein can be understood to be any RF or other signal type that has insufficient energy to seal the tissue but that is applied with a varying frequency and with enough energy to produce a return signal that is suitable to detect a center frequency. In one example, the non-therapeutic signal can have a peak-to-peak voltage of about 10V and a variable frequency range between about 200 kHz and 2 MHz. The therapeutic signal can be understood to be any RF signal that is capable of delivering sufficient energy to cause sealing of tissue that is clamped between electrodes (194, 196) of electrosurgical instrument (100). The non-therapeutic signal discussed herein Non-therapeutic waveform generator (302) and therapeutic waveform generator (304) can be in electrical communication with a switcher (306) that switches or alternates between the non-therapeutic and therapeutic signals that are delivered to the tissue from electrosurgical instrument (100). In one configuration, waveform generator (200) illustrated in FIG. 1 can include non-therapeutic waveform generator (302), therapeutic waveform generator (304), and switcher (306).

Waveform generators (302, 304) and switcher (306) can be in communication with a controller (308) that can control operation of each generator (302, 304) independently to selectively apply either the non-therapeutic or therapeutic signal to the tissue depending upon the desired application. For example, when the non-therapeutic waveform is to be applied to tissue (e.g., to conduct a preliminary analysis of the tissue), controller (308) can activate non-therapeutic waveform generator (302) and can actuate switcher (306) to facilitate connection of non-therapeutic waveform generator (302) to electrosurgical instrument (100). The resulting non-therapeutic waveform that is generated can accordingly be routed through the switcher (306) and to the electrosurgical instrument (100). When a therapeutic waveform is to be applied to tissue (e.g., to seal the tissue), controller (308) can activate therapeutic waveform generator (304) and can actuate switcher (306) to connect therapeutic waveform generator (304) to electrosurgical instrument (100). The resulting therapeutic waveform that is generated can accordingly be routed through switcher (306) and to electrosurgical instrument (100). It is to be appreciated that switcher (306) can be configured such that when a connection is made to either one of the waveform generators (302, 304), the connection to the opposing waveform generator is simultaneously disconnected to prevent the circuitry associated therewith from interfering with the integrity of the applied waveform (e.g., preventing back feed).

Controller (308) can be a general purpose controller or an application specific controller. In one example, controller (308) can be a PXI-type controller from National Instruments. Controller (308) can include a processor (not shown) that is configured to perform the necessary operations for implementing the center frequency based processes and algorithms described herein. As used herein, the term "processor" shall be understood to include a microprocessor, a micro controller, a field programmable gate array (FPGA) device, and/or any other suitable kind(s) of hardware configured to process electrical signals.

Still referring to FIG. 15, EIS system (300) can include a voltage sensor (310) and a current sensor (312) that are associated with a signal line (314) that is routed between non-therapeutic waveform generator (302) and switcher (306). Signal line (314) can facilitate delivery of the non-therapeutic waveform from non-therapeutic waveform generator (302) to the switcher (306). Voltage and current sensors (310, 312) can be configured to sense the voltage and current, respectively of the non-therapeutic waveform and the return signal present on signal line (314). In one example, voltage sensor (310) can be a voltage differential probe and current sensor (312) can be a core-type current transformer but it is to be appreciated that any of a variety of suitable alternative sensor arrangements are contemplated.

Sensors (310, 312) can be in signal communication with an oscilloscope (316) via data lines (318, 320) to facilitate delivery of the sensed voltage and current of the non-therapeutic waveform and return signal (as sensor data) to oscilloscope (316). Oscilloscope (316) can be in signal communication with controller (308) via a data line (322). Controller (308) and oscilloscope (316) can collectively be referred to as a control unit. During delivery of a non-therapeutic signal over signal line (314), oscilloscope (316) can gather the sensor data from voltage and current sensors (310, 312) via data lines (318, 320) to generate representative voltage and current waveforms of the non-therapeutic and return signals. Using those representative waveforms, oscilloscope (316) can cooperate with controller (308) to analyze the voltage and current waveforms to determine the center frequency of the system. In particular, oscilloscope (316) can calculate the phase shift of the return signal during the variation of the frequency of the non-therapeutic signal and can transmit the calculated phase shift to controller (308). As the phase shift changes, controller (308) can monitor the frequency of the non-therapeutic signal via an input (324) from non-therapeutic waveform generator (302). When the phase shift is at a minimum (e.g., zero), controller (308) can identify the frequency of the non-therapeutic signal that causes the minimum phase shift as the center frequency which can then be used to generate the therapeutic signal as well as to determine the effectiveness of the resulting tissue seal, as will be described further below.

EIS system (300) can further include a voltage sensor (326) and a current sensor (328) that are associated with a signal line (330) that is routed between therapeutic waveform generator (304) and switcher (306). Signal line (330) can facilitate delivery of the therapeutic waveform from therapeutic waveform generator (304) to the switcher (306). Voltage and current sensors (326, 328) can be configured to sense the voltage and current, respectively of the therapeutic waveform present on signal line (330). In one example, voltage sensor (326) can be a voltage differential probe and current sensor (328) can be a core-type current transformer but it is to be appreciated that any of a variety of suitable alternative sensor arrangements are contemplated.

Sensors (326, 328) can be in signal communication with oscilloscope (316) via data lines (332, 334) to facilitate delivery of the sensed voltage and current of the therapeutic waveform to oscilloscope (316). During delivery of the therapeutic signal over signal line (330), oscilloscope (316) can gather the sensor data from voltage and current sensors (26, 328) via data lines (332, 334) to generate representative voltage and current waveforms of the non-therapeutic and return signals. Oscilloscope (316) can cooperate with controller (308) to provide a feedback loop for controlling the therapeutic signal to a desired parameter or set of parameters (voltage, current, phase, power, etc.) based upon the detected voltage and/or current.

In some versions, EIS system (300) can be integrated into electrosurgical device (100) and/or waveform generator (200). In other versions EIS system (300) can be a stand-alone device that can be added to legacy equipment to add the features and methods described herein to the legacy equipment. It should be understood that EIS system (300) represents just one example hardware/software configuration for calculating a center frequency of a system from a non-therapeutic waveform, and that any of a variety of suitable hardware/software configurations that exist now or in the future can be utilized to calculate a center frequency in accordance with the methods and principles disclosed herein.

B. Method of Applying Non-Therapeutic Signal with Frequency Sweep Before Sealing Operation to Optimize Therapeutic Signal and Before and After Sealing Operation to Confirm Seal Quality In some instances, it may be desirable to optimize the characteristics of a therapeutic signal for a specific tissue impedance. For example, prior to application of a therapeutic signal, it might be desirable to first determine the overall tissue impedance of a system and then configure the parameters of the therapeutic signal to optimize the delivery of energy through the tissue. In addition, or alternatively, it may be desirable to confirm the effectiveness of a tissue seal upon completion of a sealing procedure with an electrosurgical device. For example, it may be desirable to interrogate the impedance of the tissue before and after a sealing procedure to confirm the effectiveness of the seal as a function of the change in impedance.

Figure 16:
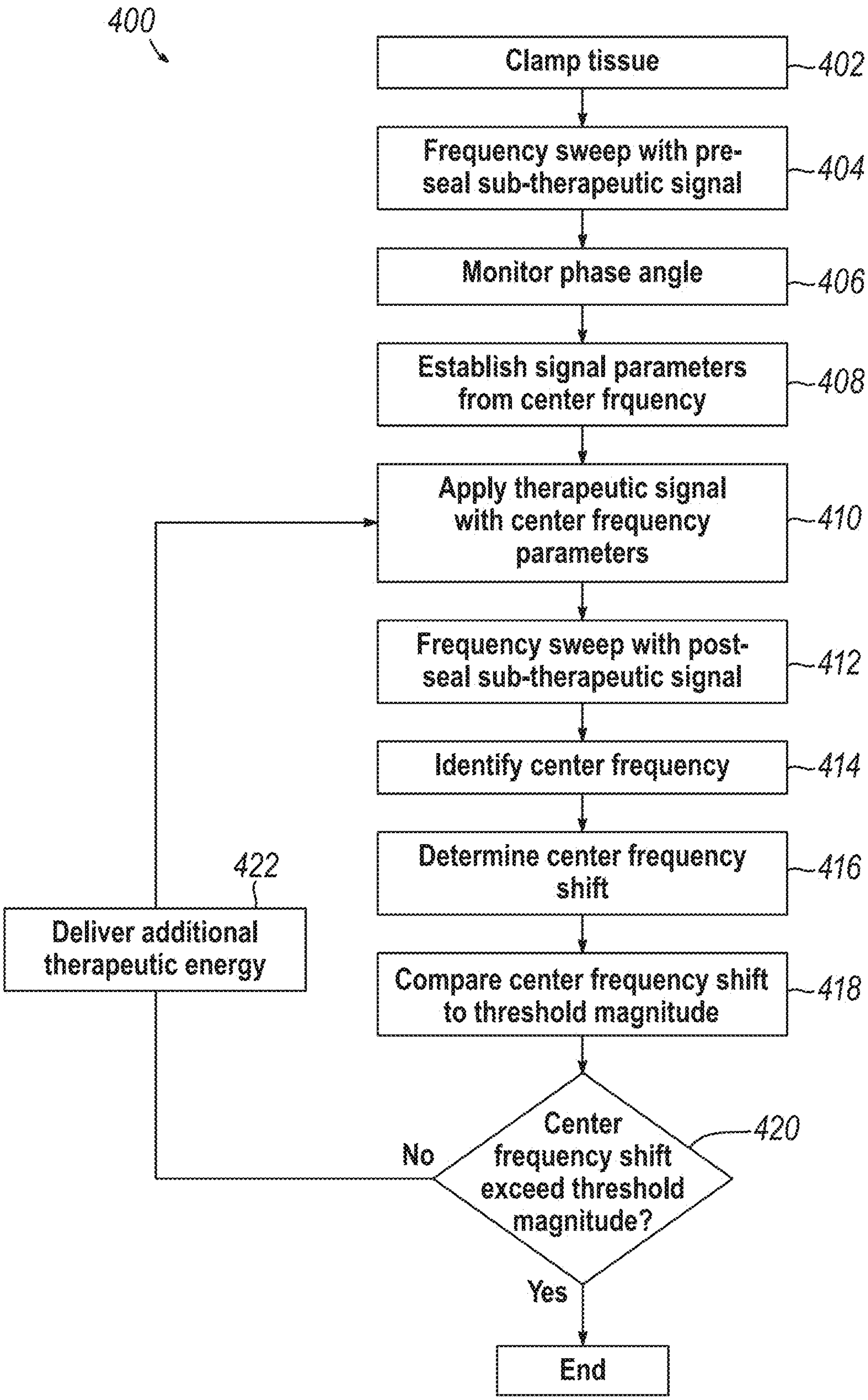
FIG. 16 depicts a flowchart of a method for interrogating a tissue with a non-therapeutic waveform to identify a center frequency of the tissue before and after application of a therapeutic waveform.
Figure 17:
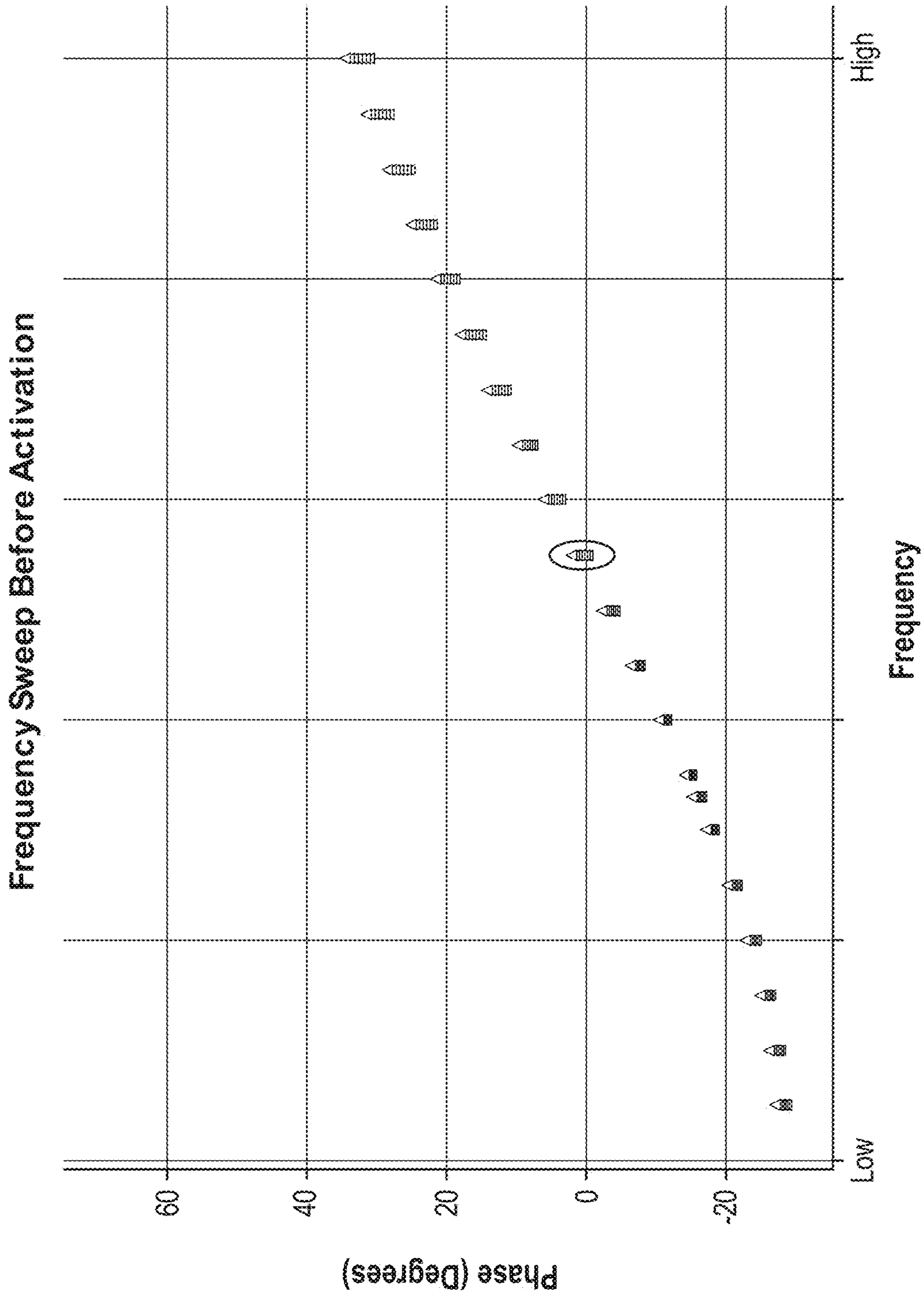
FIG. 17 depicts a scatter plot of data points from a pre-seal non-therapeutic signal.
Figure 18:
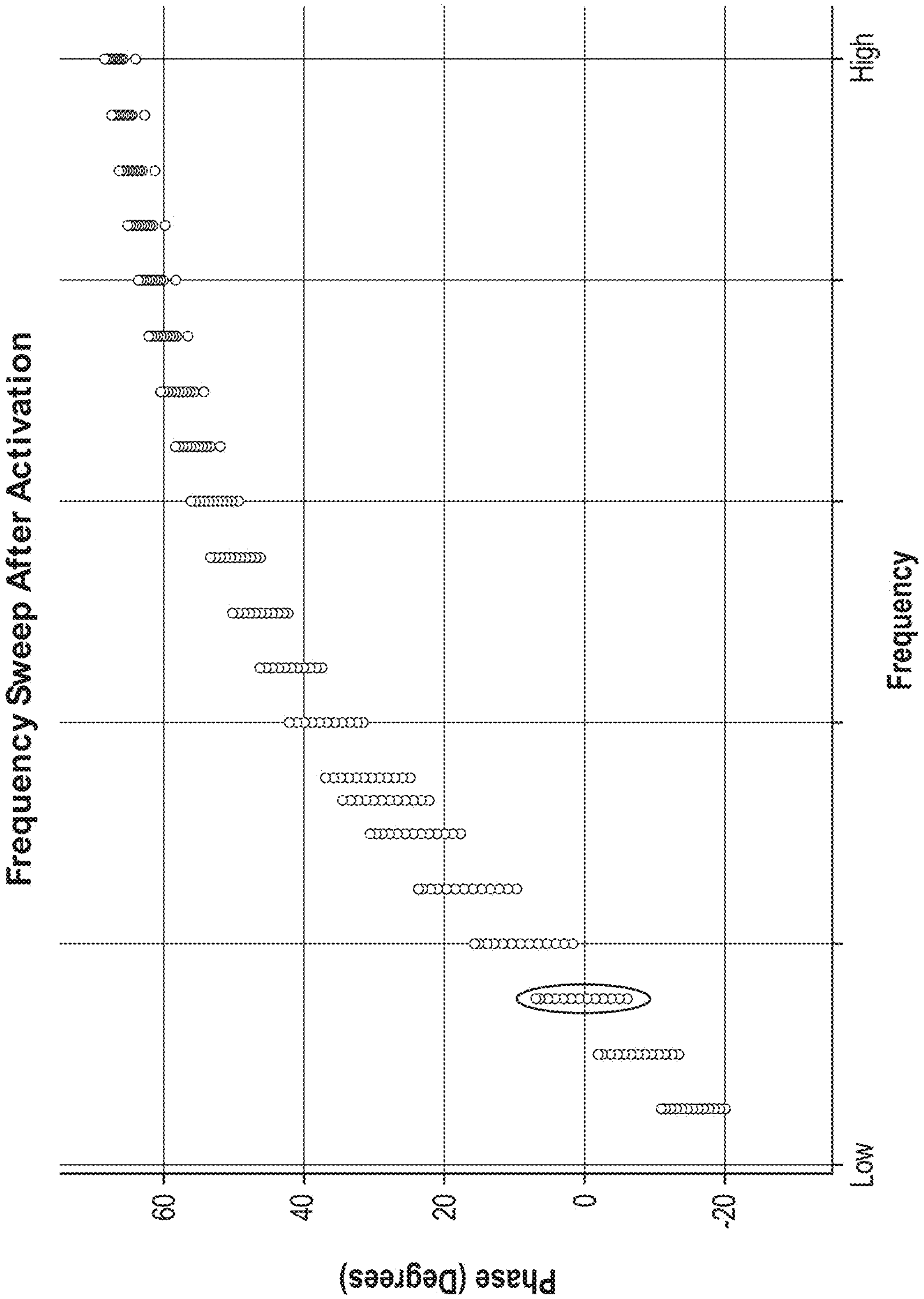
FIG. 18 depicts a scatter plot of data points from a post-seal non-therapeutic signal.
Figure 19:
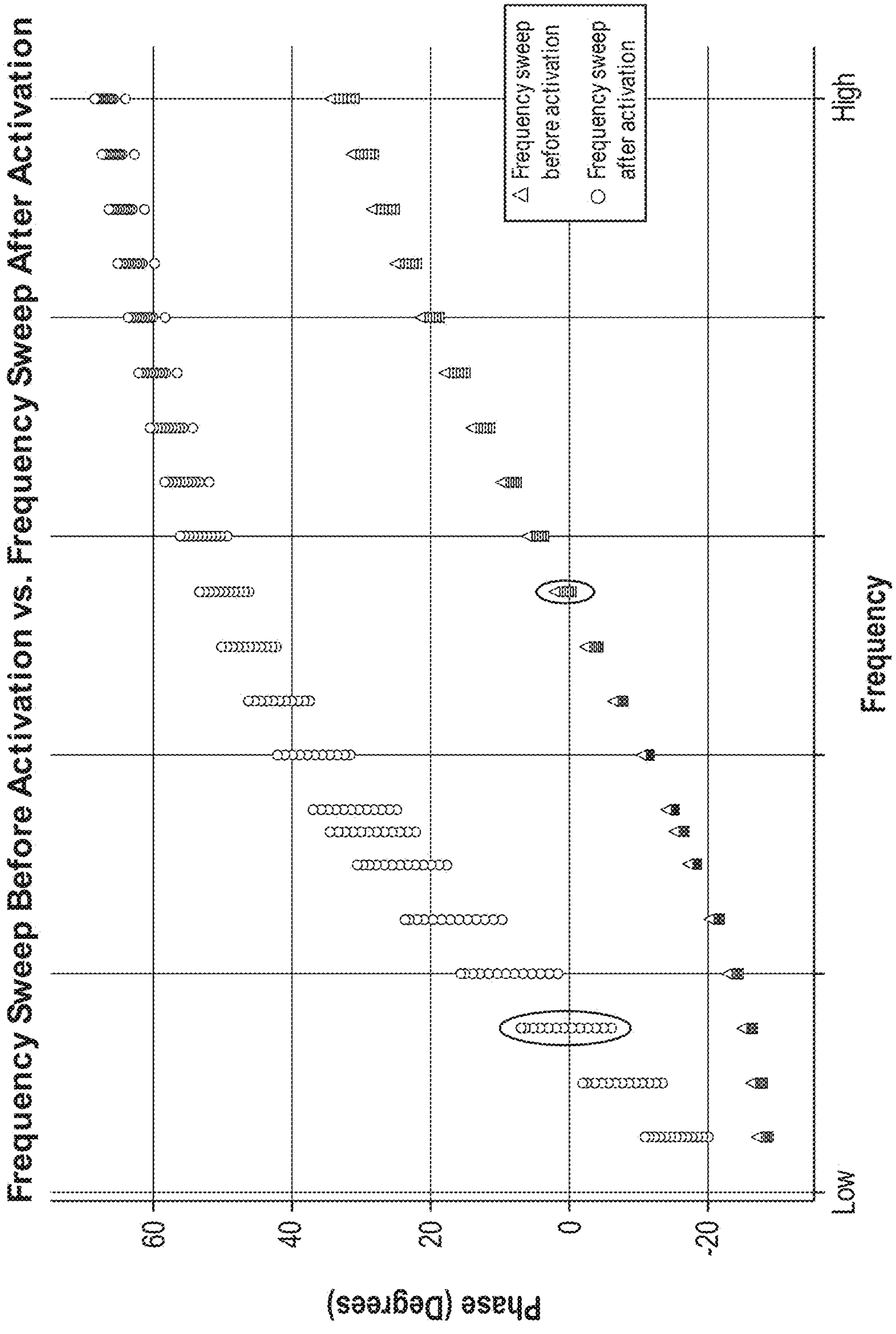
FIG. 19 depicts a scatter plot of the combined data points from FIGS. 17 and 18.

FIG. 16 shows an example of a tissue interrogation method (400) that may provide one or more such functionalities. FIGS. 17-19 aid in illustrating method (400) and will therefore be referred to during the discussion of method (400). First, the tissue can be clamped (402) between jaws (182, 184) of electrosurgical device. Once the tissue is successfully clamped, as confirmed from a clamp detection sensor or other similar type device, a pre-seal non-therapeutic signal can be applied to the tissue prior to commencing with the surgical procedure. In some examples, the pre-seal non-therapeutic signal can be applied to the tissue automatically in response to confirmation that jaws (182, 184) are properly clamped together, in response to a surgeon activating activation button (130) to initiate the application of the therapeutic waveform, or in response to firing of the knife (via knife trigger (128)).

The pre-seal non-therapeutic signal can have a substantially stable voltage and current but a frequency that is varied along a predefined range (as a frequency sweep) (404) during the application thereof. The application of the pre-seal non-therapeutic signal can be relatively short and in some instances can occur for about 10-20 mS. The non-therapeutic signal can induce a return signal from the system that has a voltage and current. The phase angle between the voltage and current of the return signal can vary as a function of the varying frequency. The varying phase angle can be monitored (406) to establish the center frequency (408) as the frequency where the phase angle is at a minimum (e.g., at zero or closest to zero). In some examples, multiple frequency sweeps can be conducted over the same range to enhance the accuracy of the center frequency. When multiple frequency sweeps are conducted, the center frequency can be understood to be the average of all the center frequencies that were identified.

In one example, the frequency sweep can be applied as a plurality of discrete frequency pulses along a predefined range. Each discrete frequency pulse can produce a corresponding phase angle of the return signal which can be monitored over time. The discrete frequency pulse that produced a minimum phase angle (e.g., closest to zero) can be identified as the center frequency. FIG. 17 depicts a graph which includes an illustrative scatter plot of the phase response of a return signal to different frequency pulses from a pre-seal non-therapeutic signal that is applied to an example system. Each frequency pulse and corresponding phase angle is represented as a triangular data point on the plot. As can be appreciated from the plot, the data points are the results of multiple frequency sweeps conducted along a low to high frequency range with each frequency sweep including 21 different discrete frequency pulses. The center frequency of the pre-sealed tissue is defined by the data points that are shown encircled on the plot.

Once the center frequency has been identified, the pre-seal non-therapeutic signal can be deactivated. The surgical procedure can then commence by firing the knife and subsequently applying the therapeutic signal at the center frequency identified during the current sweep (410). Application of the therapeutic signal at the center frequency results in an overall tissue impedance that is particularly receptive to current flow which can enhance the effectiveness of the resulting seal. It is to be appreciated that other parameters of the therapeutic signal (e.g., voltage, current, energy, waveform shape) can be selected based on the center frequency to further enhance the delivery of therapeutic energy to the surgical site.

Once the knife is retracted, the therapeutic signal can be deactivated per the direction of the surgeon. Prior to jaws 182, 184 being opened, a post-seal non-therapeutic signal can be applied to the sealed tissue (412). The post-seal non-therapeutic signal can have substantially the same parameters (e.g., voltage, current, and frequency sweep) as the pre-seal non-therapeutic signal. The center frequency of the sealed tissue can be identified (414) in a similar manner as described above for identifying the center frequency of the pre-sealed tissue. As described above, because the impedance of the tissue changes during sealing, the center frequency of the sealed tissue will be different than the center frequency of the pre-sealed tissue.

FIG. 18 depicts a graph which includes an illustrative scatter plot of the phase response of a return signal to different frequency pulses from a post-seal non-therapeutic signal that is applied to the tissue of the example system from FIG. 17. Each frequency pulse and corresponding phase angle is represented as a circular data point on the plot. As can be appreciated from the plot, the same amount of frequency sweeps can be conducted over the same frequency range using the same quantity and magnitude of the discrete frequency pulses as the pre-seal non-therapeutic signal shown in FIG. 17. The center frequency of the sealed tissue is defined by the encircled data points. FIG. 19 is a scatter plot that shows the data points from FIG. 17 and FIG. 18 on the same plot to illustrate how the center frequency of the sealed tissue is less than the center frequency of the pre-sealed tissue (both center frequencies shown encircled).

The relative difference between the center frequency of the sealed tissue and the center frequency of pre-sealed tissue (e.g., the center frequency shift) can indicate whether the tissue has been sealed properly. Referring again to FIG. 16, the center frequency of the sealed tissue can be compared with the center frequency of the pre-sealed tissue to determine the center frequency shift that resulted from sealing the tissue (416). The center frequency shift can then be compared to a threshold magnitude (418) that indicates whether the tissue has been sealed properly. The particular threshold magnitude that is used to determine whether the tissue has been sealed properly can be calculated based on a variety of different factors such as, for example, the type of tissue being sealed, the capabilities of electrosurgical device (100), the energy applied to the tissue by the therapeutic signal, and/or the amount of pressure applied by jaws (182, 184). The threshold magnitude can be predetermined or can be determined in real time (e.g., once the tissue is clamped between jaws (182, 184). In one example, the threshold magnitude can be determined from a regression model of the tissue.

If the center frequency shift meets or exceed the threshold magnitude (420), the surgical procedure can be considered complete and jaws (182, 184) can be opened to release the tissue. If the center frequency shift is less than the threshold magnitude, the tissue seal can be considered incomplete and a notification can be provided to the surgeon to deliver additional therapeutic energy to the surgical site to further seal the tissue (424). Once the additional energy has been applied to the surgical site (410), the center frequency of the sealed tissue is again identified (414) and the process for confirming whether the center frequency shift meets or exceed the threshold magnitude (416, 418, 422) is repeated until the surgical procedure is considered complete (420).

C. Method of Applying Non-Therapeutic Signal with Frequency Sweep During Sealing to Confirm Seal Quality In some instances, it may be desirable to confirm the effectiveness of a tissue seal during a sealing procedure with an electrosurgical device. For example, it may be desirable to interrogate the impedance of the tissue during a sealing procedure to confirm the effectiveness of the seal as a function of the change in impedance.

Figure 20:
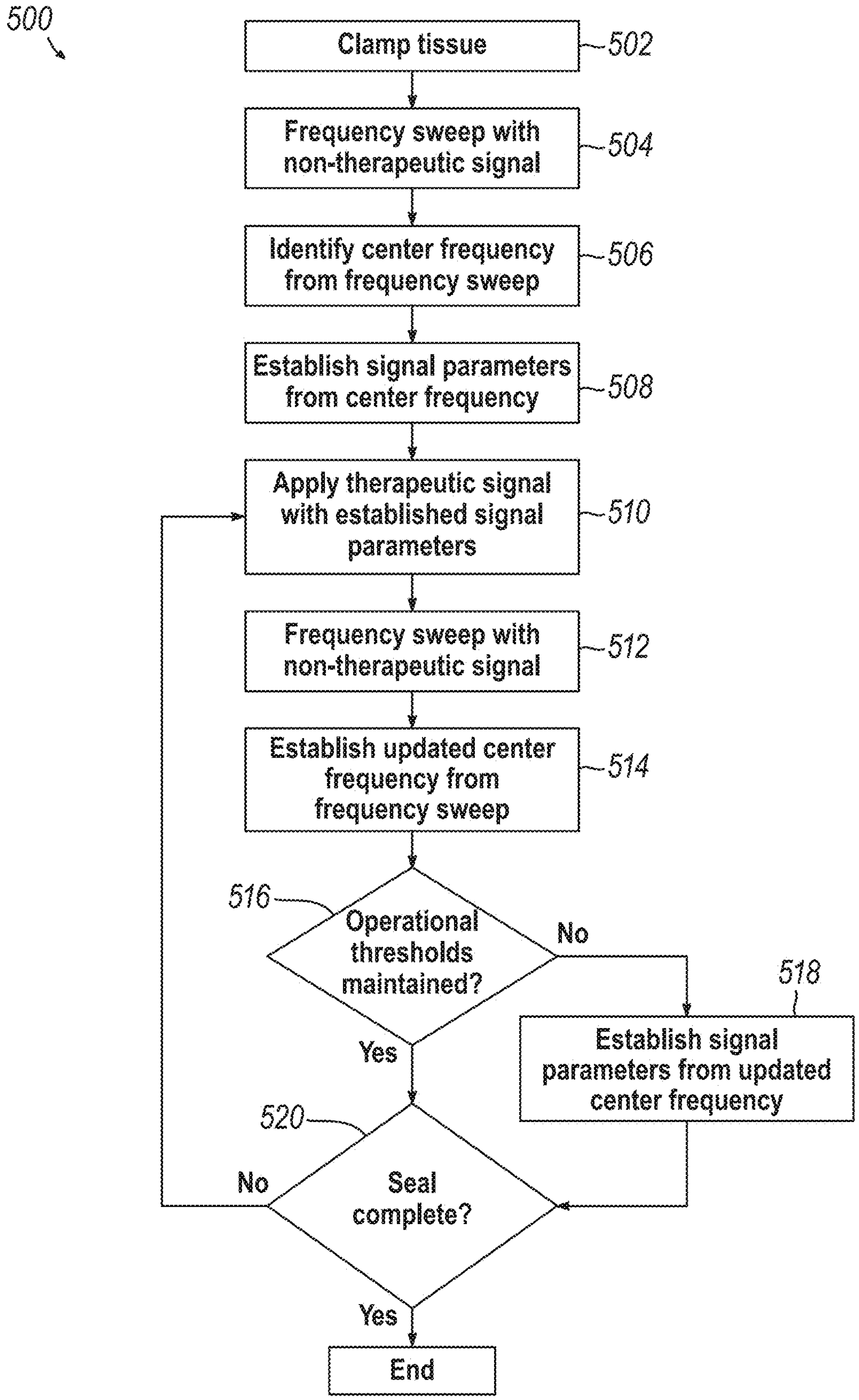
FIG. 20 depicts a flowchart of a method for interrogating a tissue with a non-therapeutic waveform to identify a center frequency of the tissue during application of a therapeutic waveform.

FIG. 20 shows an example of a tissue interrogation method (500) that may provide one or more such functionalities. The method (500) described herein incorporates many of the same techniques described above and can be understood to execute those techniques in a similar manner.

First, the tissue can be clamped (502) between jaws (182, 184) of electrosurgical device. Once the tissue is successfully clamped, as confirmed from a clamp detection sensor or other similar type device, a non-therapeutic signal can be applied to the tissue prior to commencing with the surgical procedure and can conduct a frequency sweep along a predefined range (504). A center frequency can be identified (506) for the resulting return signal as a function of the phase angle between the voltage and current of the return signal. Once the center frequency has been identified, the non-therapeutic signal can be deactivated and various signal parameters of the therapeutic signal (e.g., frequency, voltage, current, energy, waveform shape) can be established (508) based on the center frequency to optimize the delivery of the therapeutic signal to the tissue. In one example, the center frequency can be established as the frequency of the therapeutic signal.

The surgical procedure can then commence by firing the knife and subsequently applying the therapeutic signal with the established signal parameters for the therapeutic waveform (510) to begin sealing the tissue. Once the sealing of the tissue has commenced, the non-therapeutic signal can again be applied to the tissue and can conduct a frequency sweep (512). In one example, the application of the therapeutic signal can be temporarily halted (i.e., deactivated) while the non-therapeutic signal is applied to the tissue. In another example, the non-therapeutic signal can be applied to the tissue simultaneously with the application of the therapeutic signal. In any event, an updated center frequency can be calculated from the frequency sweep (514) for the present state of the impedance of the tissue.

One or more operational characteristics of the system and the tissue can then be analyzed to determine whether the operational characteristic(s) have degraded beyond a predefined threshold (516) such that the sealing of the tissue might be adversely affected by continuing to seal the tissue with the current therapeutic signal. The operational characteristics of the system and the tissue can include, for example, therapeutic signal voltage, therapeutic signal current, tissue impedance, heat, seal quality factor, electrical parameters established by a sealing algorithm. If any of the operational characteristics have degraded beyond the relevant predefined threshold, new signal parameters of the therapeutic signal can be established based on the updated center frequency (518). If the seal is not complete (520), the therapeutic signal can be updated with the new signal parameters and applied to the tissue (510) at which point the process for identifying a new center frequency (512, 514, 516) is repeated. If the operational characteristics of the system and the tissue have not degraded beyond the relevant predefined threshold, and the seal is not complete (520), the signal parameters of the therapeutic signal can be maintained. Steps (510, 512, 514, 516, 518) can be continuously repeated throughout the sealing process to enhance the effectiveness of the therapeutic signal in sealing the tissue until the seal is complete (520). In one example, the completion of the seal can be determined in a similar manner as described with respect to steps (416, 418, 422) of method (400) in FIG. 16.

IV. Illustrative Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method for performing an electrosurgical procedure using a surgical system, wherein the surgical system includes an electrosurgical instrument having an electrode configured to operate on a tissue of a patient, the method comprising: (a) engaging the tissue with the electrode; (b) applying a first non-therapeutic signal to the tissue via the electrode; (c) varying a frequency of the first non-therapeutic signal; (d) receiving a first return signal generated from the tissue in response to the first non-therapeutic signal, the first non-therapeutic signal comprising a voltage and a current; (e) detecting a phase angle between the voltage and the current of the first non-therapeutic signal during the varying of the frequency of the first non-therapeutic signal; (f) identifying, as a first center frequency, the frequency when the phase angle of the first return signal is at a minimum; and (g) applying a therapeutic signal to the tissue at the first center frequency via the electrode.

Example 2

The method of Example 1 wherein varying the frequency of the first non-therapeutic signal comprises conducting a frequency sweep.

Example 3

The method of Example 2 wherein conducting a frequency sweep comprises applying a plurality of discrete frequency pulses along a predefined range.

Example 4

The method of Example 3 wherein applying the first non-therapeutic signal is in response to activation of the electrode.

Example 5

The method of any one or more of Examples 1 through 4 further comprising deactivating the first non-therapeutic signal prior to applying the therapeutic signal.

Example 6

The method of Example 5 further comprising: (a) deactivating the therapeutic signal; (b) applying a second non-therapeutic signal to the tissue via the electrode; (c) varying a frequency of the second non-therapeutic signal; (d) receiving a second return signal generated from the tissue in response to the second non-therapeutic signal, the second non-therapeutic signal comprising a voltage and a current; (e) detecting a phase angle between the voltage and the current of the second non-therapeutic signal during the varying of the frequency of the second non-therapeutic signal; (f) identifying, as a second center frequency, the frequency when the phase angle of the second non-therapeutic signal is at a minimum; and (g) detecting a characteristic of the tissue based upon the first center frequency and the second center frequency.

Example 7

The method of Example 6 wherein the characteristic of the tissue comprises a seal quality.

Example 8

The method of Example 7 wherein detecting a characteristic of the tissue comprises: (a) comparing the first center frequency and the second center frequency; (b) determining a center frequency shift from the comparison of the first center frequency and the second center frequency; and (c) comparing the center frequency shift to a minimum threshold magnitude.

Example 9

The method of Example 8 further comprising notifying a user when the center frequency shift does not meet or exceed the minimum threshold value.

Example 10

The method of any one or more of Examples 6 through 9 wherein varying the frequency of the second non-therapeutic signal comprises conducting a frequency sweep.

Example 11

The method of Example 10 wherein conducting a frequency sweep comprises applying a plurality of discrete frequency pulses along a predefined range.

Example 12

The method of any one or more of Examples 6 through 11 wherein the first non-therapeutic signal and the second non-therapeutic signal are substantially the same.

Example 13

The method of any one or more of Examples 5 through 12 further comprising, after application of the therapeutic signal to the tissue has commenced: (a) applying a second non-therapeutic signal to the tissue via the electrode; (b) varying a frequency of the second non-therapeutic signal; (c) receiving a second return signal generated from the tissue in response to the second non-therapeutic signal, the second non-therapeutic signal comprising a voltage and a current; (d) detecting a phase angle between the voltage and the current of the second non-therapeutic signal during the varying of the frequency of the second non-therapeutic signal; (e) identifying, as a second center frequency, the frequency when the phase angle of the second non-therapeutic signal is at a minimum; (f) establishing a signal parameter for the therapeutic signal based upon the second center frequency; (g) analyzing an operational characteristic of the system to determine whether the operational characteristic have degraded beyond a predefined threshold; and (h) when the operational characteristic has degraded beyond the predefined threshold, updating the therapeutic signal with the signal parameter.

Example 14

A method for performing an electrosurgical procedure using a surgical system, wherein the surgical system includes an electrosurgical instrument having an electrode configured to operate on a tissue of a patient, the method comprising: (a) engaging the tissue with the electrode; (b) applying a therapeutic signal to the tissue; (c) applying a non-therapeutic signal to the tissue via the electrode; (d) varying a frequency of the non-therapeutic signal; (e) receiving a return signal generated from the tissue in response to the non-therapeutic signal, the non-therapeutic signal comprising a voltage and a current; (f) detecting a phase angle between the voltage and the current of the non-therapeutic signal during the varying of the frequency of the non-therapeutic signal; (g) identifying, as a center frequency, the frequency when the phase angle of the non-therapeutic signal is at a minimum; (h) establishing a signal parameter for the therapeutic signal based upon the center frequency; (i) analyzing an operational characteristic of the system to determine whether the operational characteristic have degraded beyond a predefined threshold; and (j) when the operational characteristic has degraded beyond the predefined threshold, updating the therapeutic signal with the signal parameter.

Example 15

The method of Example 14 further comprising temporarily deactivating the therapeutic signal while the non-therapeutic signal is applied to the tissue.

Example 16

The method of any one or more of Examples 14 through 15 wherein the signal parameter comprises one or more of a frequency, a voltage, a current, an energy, or a waveform shape.

Example 17

The method of any one or more of Examples 14 through 16 wherein the operational characteristic comprises one or more of a therapeutic signal voltage, a therapeutic signal current, a tissue impedance, heat, a seal quality factor, or an electrical parameter established by a sealing algorithm.

Example 18

A surgical system for performing an electrosurgical procedure, the surgical system comprising: an end effector comprising jaws configured to transition between an opened condition and a closed condition; a plurality of electrodes a positioned within the jaws of the end effector and configured to operate on a tissue of a patient; one or more waveform generators configured to apply a therapeutic signal and non-therapeutic signal to the tissue via the plurality of electrodes; and a control unit configured to store an algorithm configured to cause the control unit to: (a) apply a first non-therapeutic signal to the tissue via the one or more waveform generators; (b) vary a frequency of the first non-therapeutic signal; (c) receive a first return signal generated from the tissue in response to the first non-therapeutic signal, the first non-therapeutic signal comprising a voltage and a current; (d) detect a phase angle between the voltage and the current of the first non-therapeutic signal during the varying of the frequency of the first non-therapeutic signal; (e) identify, as a first center frequency, the frequency when the phase angle of the first return signal is at a minimum; and (f) apply a therapeutic signal to the tissue at the first center frequency via the electrode.

Example 19

The surgical system of Example 18 wherein the control unit being configured to vary the frequency of the first non-therapeutic signal further comprises the control unit being configured to apply a plurality of discrete frequency pulses along a predefined range.

Example 20

The surgical system of any one or more of Examples 18 through 19 wherein the control unit is further configured to deactivate the first non-therapeutic signal prior to application of the therapeutic signal.

V. Miscellaneous

Any one or more of the teaching, expressions, embodiments, examples, etc. described herein may be combined with any one or more of the teachings, expressions, embodiments, examples, etc. described in U.S. patent application Ser. No. 18/783,643, entitled "Electrosurgical Instrument with Impedance Spectroscopy and Method of Monitoring State of Instrument Jaws and Tissue," filed on Jul. 25, 2024; U.S. patent application Ser. No. 18/783,668, entitled "Electrosurgical Instrument with Jaw Status Monitoring and Method of Adjusting Energy Activation," filed on Jul. 25, 2024; U.S. patent application Ser. No. 18/783,680, entitled "Electrosurgical Instrument and Method of Monitoring Clamp Position to Adjust Energy Application," filed on Jul. 25, 2024; U.S. patent application Ser. No. 18/783,696, entitled "Electrosurgical Instrument and Method of Detecting Tissue Accumulation on End Effector," filed on Jul. 25, 2024; and/or U.S. patent application Ser. No. 18/783,721, entitled "Electrosurgical Instrument and Method of Applying Energy," filed on Jul. 25, 2024. The disclosure of each of these applications is incorporated by reference herein.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein, in its entirety.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for performing an electrosurgical procedure using a surgical system, wherein the surgical system includes an electrosurgical instrument having an electrode configured to operate on a tissue of a patient, the method comprising:

(a) engaging the tissue with the electrode;

(b) applying a first non-therapeutic signal to the tissue via the electrode;

(c) varying a frequency of the first non-therapeutic signal through a plurality of frequencies;

(d) receiving a first return signal generated from the tissue in response to the first non-therapeutic signal, the first non-therapeutic signal comprising a voltage and a current;

(e) detecting a plurality of phase angles between the voltage and the current of the first non-therapeutic signal respectively at the plurality of frequencies during the varying of the frequency of the first non-therapeutic signal, wherein the plurality of phase angles includes a range from a positive phase angle to a negative phase angle;

(f) identifying, as a first center frequency, the frequency of the plurality of frequencies when a magnitude of the respective phase angle of the first return signal is at a minimum; and (g) applying a therapeutic signal to the tissue at the first center frequency via the electrode.

2. The method of claim 1 wherein varying the frequency of the first non-therapeutic signal comprises conducting a frequency sweep through the plurality of frequencies.

3. The method of claim 2 wherein conducting the frequency sweep comprises applying a plurality of discrete frequency pulses along a predefined range comprising the plurality of frequencies.

4. The method of claim 3 wherein applying the first non-therapeutic signal is in response to activation of the electrode.

5. The method of claim 1 further comprising deactivating the first non-therapeutic signal prior to applying the therapeutic signal.

6. The method of claim 5 further comprising:

(a) deactivating the therapeutic signal;

(b) applying a second non-therapeutic signal to the tissue via the electrode;

(c) varying a frequency of the second non-therapeutic signal through a second plurality of frequencies;

(d) receiving a second return signal generated from the tissue in response to the second non-therapeutic signal, the second non-therapeutic signal comprising a voltage and a current;

(e) detecting a second plurality of phase angles between the voltage and the current of the second non-therapeutic signal respectively at the second plurality of frequencies during the varying of the frequency of the second non-therapeutic signal;

(f) identifying, as a second center frequency, the frequency of the second plurality of frequencies when a magnitude of the respective phase angle of the second non-therapeutic signal is at a minimum; and (g) detecting a characteristic of the tissue based upon the first center frequency and the second center frequency.

7. The method of claim 6 wherein the characteristic of the tissue comprises a seal quality.

8. The method of claim 7 wherein detecting the characteristic of the tissue comprises:

(a) comparing the first center frequency and the second center frequency;

(b) determining a center frequency shift from the comparison of the first center frequency and the second center frequency; and (c) comparing the center frequency shift to a minimum threshold magnitude.

9. The method of claim 8 further comprising notifying a user when the center frequency shift does not meet or exceed the minimum threshold value.

10. The method of claim 6 wherein varying the frequency of the second non-therapeutic signal comprises conducting a second frequency sweep through the second plurality of frequencies.

11. The method of claim 10 wherein conducting the second frequency sweep comprises applying a plurality of discrete frequency pulses along a predefined range comprising the second plurality of frequencies.

12. The method of claim 6 wherein the first non-therapeutic signal and the second non-therapeutic signal are substantially the same.

13. The method of claim 5 further comprising, after application of the therapeutic signal to the tissue has commenced:

(a) applying a second non-therapeutic signal to the tissue via the electrode;

(b) varying a frequency of the second non-therapeutic signal through a second plurality of frequencies;

(c) receiving a second return signal generated from the tissue in response to the second non-therapeutic signal, the second non-therapeutic signal comprising a voltage and a current;

(d) detecting a second plurality of phase angles between the voltage and the current of the second non-therapeutic signal respectively at the second plurality of frequencies during the varying of the frequency of the second non-therapeutic signal;

(e) identifying, as a second center frequency, the frequency of the second plurality of frequencies when a magnitude of the respective the phase angle of the second non-therapeutic signal is at a minimum;

(f) establishing a signal parameter for the therapeutic signal based upon the second center frequency;

(g) analyzing an operational characteristic of the system to determine whether the operational characteristic has degraded beyond a predefined threshold; and (h) when the operational characteristic has degraded beyond the predefined threshold, updating the therapeutic signal with the signal parameter.

14. A method for performing an electrosurgical procedure using a surgical system, wherein the surgical system includes an electrosurgical instrument having an electrode configured to operate on a tissue of a patient, the method comprising:

(a) engaging the tissue with the electrode;
(b) applying a therapeutic signal to the tissue;
(c) applying a non-therapeutic signal to the tissue via the electrode;
(d) varying a frequency of the non-therapeutic signal between a plurality of predetermined frequencies;
(e) receiving a return signal generated from the tissue in response to the non-therapeutic signal, the non-therapeutic signal comprising a voltage and a current;
(f) detecting a phase angle between the voltage and the current of the non-therapeutic signal at each of the plurality of predetermined frequencies during the varying of the frequency of the non-therapeutic signal;
(g) after determining each phase angle, identifying, as a center frequency, the frequency when a magnitude of the phase angle of the non-therapeutic signal is at a minimum;
(h) establishing a signal parameter for the therapeutic signal based upon the center frequency;
(i) analyzing an operational characteristic of the system to determine whether the operational characteristic has degraded beyond a predefined threshold; and
(j) when the operational characteristic has degraded beyond the predefined threshold, updating and applying the therapeutic signal with the signal parameter.

15. The method of claim 14 further comprising temporarily deactivating the therapeutic signal while the non-therapeutic signal is applied to the tissue.

16. The method of claim 14 wherein the signal parameter comprises one or more of a frequency, a voltage, a current, an energy, or a waveform shape.

17. The method of claim 14 wherein the operational characteristic comprises one or more of a therapeutic signal voltage, a therapeutic signal current, a tissue impedance, heat, a seal quality factor, or an electrical parameter established by a sealing algorithm.

18. A surgical system for performing an electrosurgical procedure, the surgical system comprising:

an end effector comprising jaws configured to transition between an opened condition and a closed condition;
a plurality of electrodes a positioned within the jaws of the end effector and configured to operate on a tissue of a patient;
one or more waveform generators configured to apply a therapeutic signal and non-therapeutic signal to the tissue via the plurality of electrodes; and
a control unit configured to store an algorithm configured to cause the control unit to:
(a) apply a first non-therapeutic signal to the tissue via the one or more waveform generators;
(b) vary a frequency of the first non-therapeutic signal to include a first frequency, a second frequency, and a third frequency, the second frequency being between the first frequency and the third frequency on a frequency range;
(c) receive a first return signal generated from the tissue in response to the first non-therapeutic signal, the first non-therapeutic signal comprising a voltage and a current;
(d) detect a phase angle of each of the first, second, and third frequencies between the voltage and the current of the first non-therapeutic signal during the varying of the frequency of the first non-therapeutic signal;
(e) identify, as a first center frequency, the frequency when a magnitude of the phase angle of the first return signal is at a minimum, the first center frequency being the second frequency; and
(f) apply a therapeutic signal to the tissue at the first center frequency via at least one electrode of the plurality of electrodes.

19. The surgical system of claim 18 wherein the control unit being configured to vary the frequency of the first non-therapeutic signal further comprises the control unit being configured to apply a plurality of discrete frequency pulses along a predefined range that includes the first, second, and third frequencies.

20. The surgical system of claim 18 wherein the control unit is further configured to deactivate the first non-therapeutic signal prior to application of the therapeutic signal.

* * * * *